(12) United States Patent
Ware et al.

(10) Patent No.: US 7,765,113 B2
(45) Date of Patent: Jul. 27, 2010

(54) METHOD AND SYSTEM FOR HEALTH ASSESSMENT AND MONITORING

(75) Inventors: John E. Ware, Medfield, MA (US); Mark R. Kosinski, Sterling, MA (US); Jakob Bue Bjorner, Charlottenlund (DK); Barbara Sardinha, Portsmouth, RI (US); James E. Dewey, Narragansett, RI (US)

(73) Assignee: Qualitymetric, Inc., Lincoln, RI (US)

( * ) Notice: Subject to any disclaimer, the term of this patent is extended or adjusted under 35 U.S.C. 154(b) by 1631 days.

(21) Appl. No.: 09/873,500

(22) Filed: Jun. 4, 2001

(65) Prior Publication Data

US 2002/0019747 A1 Feb. 14, 2002

Related U.S. Application Data

(60) Provisional application No. 60/209,105, filed on Jun. 2, 2000.

(51) Int. Cl.
*A61B 5/00* (2006.01)
*G06F 19/00* (2006.01)

(52) U.S. Cl. .................. 705/3; 705/2; 705/4; 434/236; 434/322

(58) Field of Classification Search ................ 434/236, 434/322
See application file for complete search history.

(56) References Cited

U.S. PATENT DOCUMENTS

| | | | |
|---|---|---|---|
| 4,627,818 A | 12/1986 | Von Fellenberg | |
| 5,006,699 A * | 4/1991 | Felkner et al. | 235/462.49 |
| 5,059,127 A * | 10/1991 | Lewis et al. | 434/353 |
| 5,262,943 A * | 11/1993 | Thibado et al. | 600/300 |
| 5,390,238 A | 2/1995 | Kirk et al. | |
| 5,434,611 A | 7/1995 | Tamura | |
| 5,441,047 A | 8/1995 | David et al. | |
| 5,565,316 A * | 10/1996 | Kershaw et al. | 434/322 |
| 5,666,492 A | 9/1997 | Rhodes et al. | |
| 5,845,254 A | 12/1998 | Lockwood et al. | |
| 5,879,163 A | 3/1999 | Brown et al. | |
| 5,882,203 A | 3/1999 | Correa et al. | |
| 5,897,493 A | 4/1999 | Brown | |
| 5,908,301 A | 6/1999 | Lutz | |
| 5,935,060 A | 8/1999 | Iliff | |
| 5,940,801 A | 8/1999 | Brown | |
| 5,954,510 A | 9/1999 | Merrill et al. | |
| 5,961,332 A | 10/1999 | Joao | |
| 5,967,789 A | 10/1999 | Segel et al. | |
| 5,997,476 A | 12/1999 | Brown | |

(Continued)

OTHER PUBLICATIONS

John E. Ware, Jr., Ph.D et al., "Dynamic Health Assessments: The search for more practical and more precise outcome measures," Quality of Life Newsletter, No. 21 (Jan.-Apr. 1999).*

(Continued)

*Primary Examiner*—Gerald J. O'Connor
*Assistant Examiner*—Linh Michelle Le
(74) *Attorney, Agent, or Firm*—Fulbright & Jaworski

(57) ABSTRACT

The present invention relates to an assessment technique which is conveniently practiced on a computer or over a network. The assessment technique is particularly useful in assessment of health related factors. The invention also relates to a general purpose programmable computer which is provided with instructions for operating according to the assessment technique.

41 Claims, 48 Drawing Sheets

U.S. PATENT DOCUMENTS

| | | | |
|---|---|---|---|
| 6,039,688 A | | 3/2000 | Douglas et al. |
| 6,056,556 A | * | 5/2000 | Braun et al. ................ 434/323 |
| 6,059,724 A | | 5/2000 | Campell et al. |
| 6,067,523 A | * | 5/2000 | Bair et al. ...................... 705/3 |
| 6,151,581 A | * | 11/2000 | Kraftson et al. ................ 705/3 |
| 6,280,380 B1 | * | 8/2001 | Bardy ........................ 600/300 |
| 6,385,589 B1 | * | 5/2002 | Trusheim et al. ............... 705/2 |
| 6,697,783 B1 | * | 2/2004 | Brinkman et al. .............. 705/3 |

OTHER PUBLICATIONS

Ware et al. (Ware, Jr., John E., Jakob Bjorner, and Mark Kosinski, Dynamic Health Assessments: The Search for More Practical and More Precise Outcomes Measures, The Quality of Life Newsletter, Jan. 1999-Apr. 1999).*

Ware, Jr., John E., Jakob Bjorner, and Mark Kosinski, Dynamic Health Assessments: The Search for More Practical and More Precise Outcomes Measures, The Quality of Life Newsletter, Jan. 1999-Apr. 1999.*

John E. Ware, Jr., Ph.D. et al., "SF-36 Health Survey—Manual & Interpretation Guide," The Health Institute, New England Medical Center, Boston, Massachusetts (copyright, 1993).

John E. Ware, Jr.; Ph.D. et al., "Dynamic Health Assessments: The Search for More Practical and More Precise Outcomes Measures," Quality of Life newsletter, No. 21 (Jan.-Apr. 1999).

John E. Ware, Jr., Ph.D. et al., "The MOS 36-Item Short Form Health Survey (SF-36)", Medical Care, vol. 30, No. 6 (Jun. 1992).

Howard Wainer et al., "Computer Adaptive Testing—A Primer", Lawrence Erlbaum Associates, Hillsdale, New Jersey, pp. 103-135 (1990).

* cited by examiner

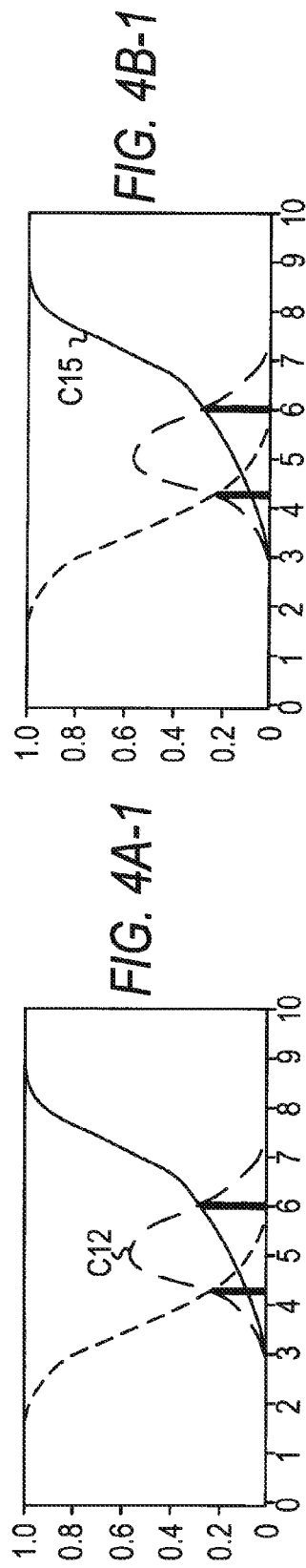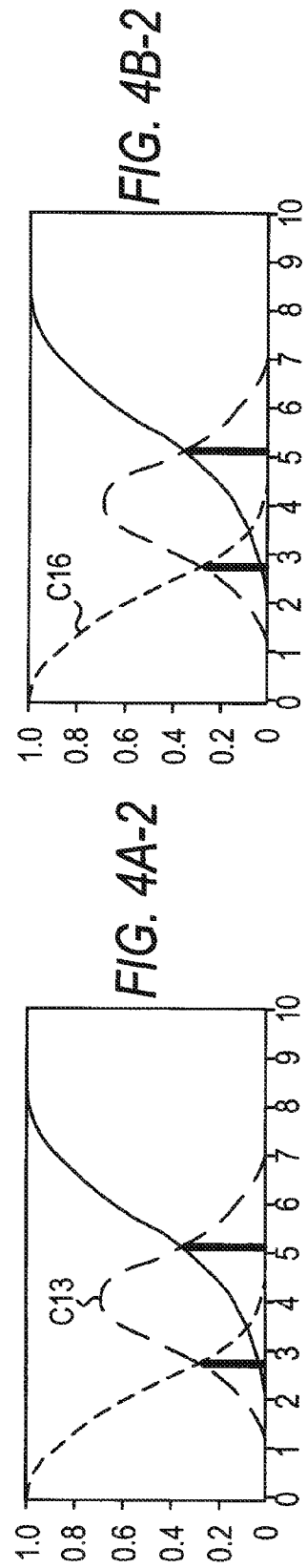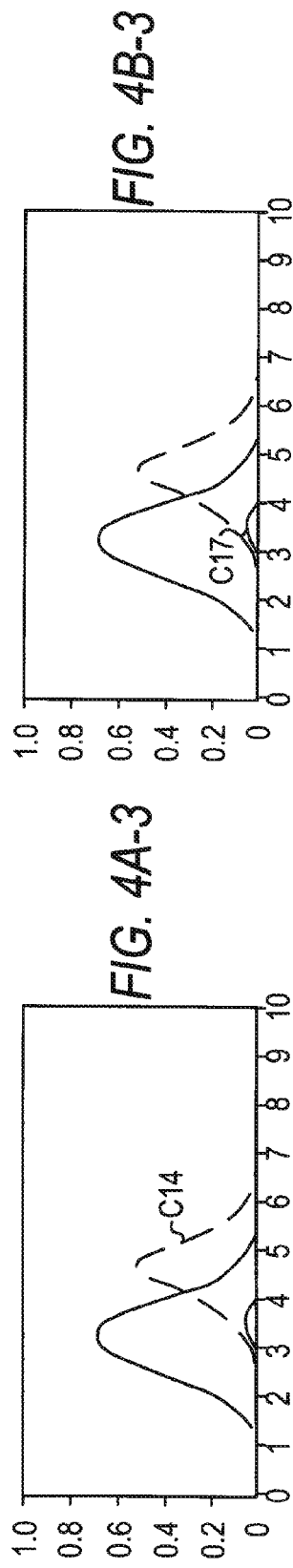

amihealthy.com™

DYNAMIC HEALTH SURVEY™

1. OVERALL, HOW WOULD YOU RATE YOUR HEALTH DURING THE PAST 4 WEEKS?

- ● EXCELLENT
- ○ VERY GOOD
- ○ GOOD
- ○ FAIR
- ○ POOR
- ○ VERY POOR

NEXT    EXIT SURVEY

FIG. 7-2

*amIhealthy.com*™

DYNAMIC HEALTH SURVEY™

2. THE FOLLOWING QUESTIONS ARE ABOUT ACTIVITIES YOU MIGHT DO DURING A TYPICAL DAY. DURING THE PAST 4 WEEKS, HOW MUCH DID PHYSICAL HEALTH PROBLEMS LIMIT YOUR USUAL PHYSICAL ACTIVITIES (SUCH AS WALKING OR CLIMBING STAIRS)?

- ⦿ NOT AT ALL
- ○ VERY LITTLE
- ○ SOMEWHAT
- ○ QUITE A LOT
- ○ COULD NOT DO PHYSICAL ACTIVITIES

[NEXT]   [EXIT SURVEY]

*FIG. 7-3*

*amIhealthy.com*™

DYNAMIC HEALTH SURVEY™

3. DURING THE PAST 4 WEEKS, HOW MUCH DIFFICULTY DID YOU HAVE DOING YOUR DAILY WORK, BOTH INSIDE AND OUTSIDE THE HOUSE, BECAUSE OF YOUR PHYSICAL HEALTH

- ◉ NOT AT ALL
- ○ VERY LITTLE
- ○ SOMEWHAT
- ○ QUITE A LOT
- ○ COULD NOT DO DAILY WORK

NEXT    EXIT SURVEY

*FIG. 7-4* amIhealthy.com™

DYNAMIC HEALTH SURVEY™

4. HOW MUCH BODILY PAIN HAVE YOU HAD DURING THE PAST 4 WEEKS?

- ◉ NONE
- ○ VERY MILD
- ○ MILD
- ○ MODERATE
- ○ SEVERE
- ○ VERY SEVERE

NEXT

EXIT SURVEY

FIG. 7-5

*amIhealthy.com*™

DYNAMIC HEALTH SURVEY™

5. THESE QUESTIONS ARE ABOUT HOW YOU FEEL AND HOW THINGS HAVE BEEN WITH YOU DURING THE PAST 4 WEEKS. FOR EACH QUESTION, PLEASE GIVE THE ONE ANSWER THAT COMES CLOSEST TO THE WAY YOU HAVE BEEN FEELING.

DURING THE PAST 4 WEEKS, HOW MUCH ENERGY DID YOU HAVE?

⦿ VERY MUCH
○ QUITE A BIT
○ SOME
○ A LITTLE
○ NONE

NEXT    NEXT    EXIT SURVEY

*FIG. 7-6*

*amIhealthy.com*™

DYNAMIC HEALTH SURVEY™

6. THE NEXT QUESTIONS ASK ABOUT YOUR SOCIAL ACTIVITIES.

DURING THE PAST 4 WEEKS, HOW MUCH DID YOUR PHYSICAL HEALTH OR EMOTIONAL PROBLEMS LIMIT YOUR USUAL SOCIAL ACTIVITIES WITH FAMILY OR FRIENDS?

- ● NOT AT ALL
- ○ VERY LITTLE
- ○ SOMEWHAT
- ○ QUITE A LOT
- ○ COULD NOT DO SOCIAL ACTIVITIES

NEXT    EXIT SURVEY

NEXT

*FIG. 7-7*

*am*Ihealthy.com™

DYNAMIC HEALTH SURVEY™

7. THESE QUESTIONS ARE ABOUT HOW YOU FEEL AND HOW THINGS HAVE BEEN WITH YOU DURING THE PAST 4 WEEKS. FOR EACH QUESTION, PLEASE GIVE THE ONE ANSWER THAT COMES CLOSEST TO THE WAY YOU HAVE BEEN FEELING.

HOW MUCH HAVE YOU BEEN BOTHERED BY EMOTIONAL PROBLEMS (SUCH AS FEELING ANXIOUS, DEPRESSED OR IRRITABLE)?

- ◉ NOT AT ALL
- ○ SLIGHTLY
- ○ MODERATELY
- ○ QUITE A LOT
- ○ EXTREMELY

NEXT   EXIT SURVEY

*FIG. 7-8*

*amIhealthy*.com™

DYNAMIC HEALTH SURVEY™

8. DURING THE PAST 4 WEEKS, HOW MUCH DID PERSONAL OR EMOTIONAL PROBLEMS KEEP YOU FROM DOING YOUR USUAL WORK, SCHOOL OR OTHER DAILY ACTIVITIES?
   - ◉ NOT AT ALL
   - ○ VERY LITTLE
   - ○ SOMEWHAT
   - ○ QUITE A LOT
   - ○ COULD NOT DO DAILY ACTIVITIES

NEXT       EXIT SURVEY

DYNAMIC HEALTH SURVEY™ — REPORT FOR ANONYMOUS

YOUR SCORES

REPORT DATE: MAY 10, 2000
AGE: UNKNOWN
GENDER: UNKNOWN
CONDITIONS: UNKNOWN

▷ PHYSICAL HEALTH SUMMARY | 57

```
      57
       ▼
|----|----|----|----|----|
30   40   50   60   70
WORST   US AVG.      BEST
```

YOUR PHYSICAL HEALTH SUMMARY SCORE IS ABOVE AVERAGE, TAKING INTO ACCOUNT THE MARGIN OF ERROR.

▷ MENTAL HEALTH SUMMARY | 56

```
      56
       ▼
|----|----|----|----|----|
30   40   50   60   70
WORST   US AVG.      BEST
```

YOUR MENTAL HEALTH SUMMARY SCORE IS ABOVE AVERAGE, TAKING ACCOUNT THE MARGIN OF ERROR.

▷ YOUR PROGRESS

| DATE | PHYSICAL HEALTH SUMMARY | MENTAL HEALTH SUMMARY |
|---|---|---|
| CURRENT: 5/10/00 | 57 | 56 |

- WE ENCOURAGE YOU TO BECOME A REGISTERED USER SO THAT WE CAN REPORT AND INTERPRET YOUR CHANGES IN SCORES OVER TIME.

? WHAT YOUR SCORES MEAN

BASED ON YOUR ANSWERS ABOUT YOUR HEALTH IN THE PAST 4 WEEKS, OUR RESEARCH SHOWS THAT:

COMPARED TO THE GENERAL POPULATION...
*PHYSICALLY*, YOUR...
- FUNCTIONING IS BETTER THAN MOST
- PAIN IS MUCH LESS
- PERFORMANCE OF WORK, HOME OR SCHOOL ACTIVITIES IS THE SAME OR BETTER

*EMOTIONALLY*...
- BOTHERED LESS THAN MOST
- PARTICIPATION IN SOCIAL ACTIVITIES IS LESS LIMITED
- PERFORMANCE OF WORK, HOME AND SCHOOL ACTIVITIES IS LIMITED LESS

*OVERALL*, YOUR...
- RATING OF YOUR HEALTH IS MUCH BETTER
- ENERGY LEVEL IS MUCH HIGHER

✎ WHAT YOU SHOULD DO

- IN THREE MONTHS, TAKE THIS SURVEY AGAIN TO CONTINUE MONITORING YOUR PROGRESS.
- BY SHOWING THIS REPORT TO YOUR DOCTOR OR OTHER HEALTH CARE PROVIDER, YOU CAN WORK TOGETHER TO MAKE SURE THAT YOUR PHYSICAL & MENTAL HEALTH ARE AS GOOD AS THEY CAN BE.

NOTE: THIS SURVEY IS NOT A DIAGNOSTIC TOOL. IT IS INTENDED TO SUPPLEMENT, BUT NOT REPLACE OR CONTRADICT THE ADVICE OF YOUR PERSONAL PHYSICIAN. IF YOU HAVE ANY QUESTIONS OR CONCERNS ABOUT YOUR HEALTH, IT IS ALWAYS A GOOD IDEA TO SEEK ONE-ON-ONE PROFESSIONAL MEDICAL CONSULTATION.

*amIhealthy.com*™

DYNAMIC HEALTH SURVEY™

THIS SURVEY ASKS YOU QUESTIONS ABOUT HOW YOUR PHYSICAL AND EMOTIONAL HEALTH AFFECT THINGS YOU DO EVERY DAY. YOU ARE THE EXPERT ON THESE ASPECTS OF YOUR OVERALL HEALTH. PLEASE ANSWER THE QUESTIONS BY CLICKING THE ANSWER THAT BEST DESCRIBES HOW YOU HAVE BEEN DOING DURING THE PAST 4 WEEKS. IF YOU ARE NOT SURE ABOUT A QUESTION, PLEASE GIVE THE BEST ANSWER YOU CAN.

CONTINUE    EXIT SURVEY

FIG. 8-1

*amIhealthy.com*™

DYNAMIC HEALTH SURVEY™

GENERAL HEALTH

1. OVERALL, HOW WOULD YOU RATE YOUR HEALTH DURING THE PAST 4 WEEKS?

○ EXCELLENT
   ○ VERY GOOD
   ○ GOOD
   ○ FAIR
   ○ POOR
   ◉ VERY POOR

NEXT    EXIT SURVEY

*FIG. 8-2*

*amIhealthy.com*™

DYNAMIC HEALTH SURVEY™

2. HOW TRUE OR FASLE IS THE FOLLOWING STATEMENT FOR YOU? I AM IN POOR HEALTH.

- ⦿ DEFINITELY TRUE
- ○ MOSTLY TRUE
- ○ DON'T KNOW
- ○ MOSTLY FALSE
- ○ DEFINITELY FASLE

NEXT   EXIT SURVEY

*FIG. 8-3*

*amIhealthy*.com™

DYNAMIC HEALTH SURVEY™

3. IN GENERAL, WOULD YOU SAY YOUR HEALTH IS:
   - ○ EXCELLENT
   - ○ VERY GOOD
   - ○ GOOD
   - ○ FAIR
   - ◉ POOR

NEXT

EXIT SURVEY

*amIhealthy.com*™

DYNAMIC HEALTH SURVEY™

5. THE FOLLOWING QUESTIONS ARE ABOUT ACTIVITIES YOU MIGHT DO DURING A TYPICAL DAY. DURING THE PAST 4 WEEKS, HOW MUCH DID PHYSICAL HEALTH PROBLEMS LIMIT YOUR USUAL PHYSICAL ACTIVITIES (SUCH AS WALKING OR CLIMBING STAIRS)?

○ NOT AT ALL
○ VERY LITTLE
○ SOMEWHAT
◉ QUITE A LOT
○ COULD NOT DO PHYSICAL ACTIVITIES

NEXT    EXIT SURVEY

*FIG. 8-6* amIhealthy.com™

DYNAMIC HEALTH SURVEY™

7. DURING THE PAST 4 WEEKS, HOW MUCH DIFFICULTY DID YOU HAVE DOING YOUR DAILY WORK, BOTH INSIDE AND OUTSIDE THE HOUSE, BECAUSE OF YOUR PHYSICAL HEALTH

○ NOT AT ALL
○ VERY LITTLE
○ SOMEWHAT
◉ QUITE A LOT
○ COULD NOT DO PHYSICAL ACTIVITIES

NEXT     EXIT SURVEY

*FIG. 8-8*

*am*Ihealthy.com™

DYNAMIC HEALTH SURVEY™

8. DURING THE PAST 4 WEEKS, HOW MUCH OF THE TIME WERE YOU LIMITED IN THE KIND OF WORK OR OTHER ACTIVITIES YOU DID AS A RESULT OF YOUR PHYSICAL HEALTH?

○ ALL OF THE TIME
◉ MOST OF THE TIME
○ SOME OF THE TIME
○ A LITTLE OF THE TIME
○ NONE OF THE TIME

NEXT    EXIT SURVEY

FIG. 8-9

*amIhealthy.com*™

DYNAMIC HEALTH SURVEY™

9. DURING THE PAST 4 WEEKS, HOW MUCH OF THE TIME HAVE YOU HAD DIFFICULTY PERFORMING WORK OR OTHER ACTIVITIES AS A RESULT OF YOUR PHYSICAL HEALTH (FOR EXAMPLE, IT TOOK EXTRA EFFORT)?

⦿ ALL OF THE TIME
○ MOST OF THE TIME
○ SOME OF THE TIME
○ A LITTLE OF THE TIME
○ NONE OF THE TIME

NEXT    EXIT SURVEY

*FIG. 8-10*

*amIhealthy*.com™

DYNAMIC HEALTH SURVEY™

10. HOW MUCH BODILY PAIN HAVE YOU HAD DURING THE PAST 4 WEEKS?

○ NONE
○ VERY MILD
○ MILD
○ MODERATE
⦿ SERVERE
○ VERY SERVERE

NEXT

EXIT SURVEY

*FIG. 8-11*

*amIhealthy.com*™

DYNAMIC HEALTH SURVEY™

11. DURING THE PAST 4 WEEKS, HOW MUCH DID PAIN INTERFERE WITH YOUR NORMAL WORK (INCLUDING BOTH WORK OUTSIDE THE HOME AND HOUSEWORK)?

○ NOT AT ALL
○ A LITTLE BIT
○ MODERATELY
○ QUITE A BIT
◉ EXTREMELY

NEXT     EXIT SURVEY

*FIG. 8-12*

*amIhealthy*.com™

DYNAMIC HEALTH SURVEY™

GENERAL HEALTH™

13. THESE QUESTIONS ARE ABOUT HOW YOU FEEL AND HOW THINGS HAVE BEEN WITH YOU DURING THE PAST 4 WEEKS. FOR EACH QUESTION, PLEASE GIVE THE ONE ANSWER THAT COMES CLOSEST TO THE WAY YOU HAVE BEEN FEELING.

DURING THE PAST 4 WEEKS, HOW MUCH ENERGY DID YOU HAVE?

○ VERY MUCH
○ QUIT A BIT
◉ SOME
○ A LITTLE
○ NONE

NEXT    EXIT SURVEY

FIG. 8-14

*amIhealthy.com*™

DYNAMIC HEALTH SURVEY™

14. HOW MUCH OF THE TIME DURING THE PAST 4 WEEKS DID YOU FEEL TIRED?
   ○ ALL OF THE TIME
   ○ MOST OF THE TIME
   ⦿ SOME OF THE TIME
   ○ A LITTLE OF THE TIME
   ○ NONE OF THE TIME

NEXT      EXIT SURVEY

FIG. 8-15 amIhealthy.com™

DYNAMIC HEALTH SURVEY™

15. HOW MUCH OF THE TIME DURING THE PAST 4 WEEKS DID YOU FELL WORN OUT?

○ ALL OF THE TIME
○ MOST OF THE TIME
◉ SOME OF THE TIME
○ A LITTLE OF THE TIME
○ NONE OF THE TIME

NEXT      EXIT SURVEY

FIG. 8-16

*amIhealthy.com*™

DYNAMIC HEALTH SURVEY™

16. HOW MUCH OF THE TIME DURING THE PAST 4 WEEKS DID YOU HAVE A LOT OF ENERGY?
   ○ ALL OF THE TIME
   ○ MOST OF THE TIME
   ⦿ SOME OF THE TIME
   ○ A LITTLE OF THE TIME
   ○ NONE OF THE TIME ( NEXT )   ( EXIT SURVEY )

FIG. 8-17

*am*Ihealthy.com™

DYNAMIC HEALTH SURVEY™

17. HOW MUCH OF THE TIME DURING THE PAST 4 WEEKS DID YOU FEEL FULL OF LIFE?
   ○ ALL OF THE TIME
   ○ MOST OF THE TIME
   ○ SOME OF THE TIME
   ⦿ A LITTLE OF THE TIME
   ○ NONE OF THE TIME

NEXT    EXIT SURVEY

FIG. 8-18

*amIhealthy.com*™

DYNAMIC HEALTH SURVEY™

18. THE NEXT QUESTIONS ASK ABOUT YOUR SOCIAL ACTIVITIES.

DURING THE PAST 4 WEEKS, HOW MUCH DID YOUR PHYSICAL HEALTH OR EMOTIONAL PROBLEMS LIMIT YOUR USUAL SOCIAL ACTIVITIES WITH FAMILY OR FRIENDS?

○ NOT AT ALL
○ VERY LITTLE
○ SOMEWHAT
○ QUITE A LOT
◉ COULD NOT DO SOCIAL ACTIVITIES

NEXT

EXIT SURVEY

*FIG. 8-19*

*amIhealthy.com*™

DYNAMIC HEALTH SURVEY™

19. DURING THE PAST 4 WEEKS, HOW MUCH OF THE TIME HAS YOUR PHYSICAL HEALTH OR EMOTIONAL PROBLEMS INTERFERED WITH YOUR SOCIAL ACTIVITIES (LIKE VISITING WITH FRIENDS, RELATIVES, ETC.)?

- ◉ ALL OF THE TIME
- ○ MOST OF THE TIME
- ○ SOME OF THE TIME
- ○ A LITTLE OF THE TIME
- ○ NONE OF THE TIME

NEXT    EXIT SURVEY

FIG. 8-20

*am*Ihealthy.com™

DYNAMIC HEALTH SURVEY™

20. DURING THE PAST 4 WEEKS, TO WHAT EXTENT HAS YOUR PHYSICAL HEALTH OR EMOTIONAL PROBLEMS INTERFERED WITH YOUR NORMAL SOCIAL ACTIVITIES WITH FAMILY, FRIENDS, NEIGHBORS, OR GROUPS?

○ NOT AT ALL
○ A LITTLE BIT
○ MODERATELY
○ QUITE A BIT
◉ EXTREMELY

NEXT    EXIT SURVEY

FIG. 8-21

*amIhealthy*™

DYNAMIC HEALTH SURVEY™

21. THESE QUESTIONS ARE ABOUT HOW OU FEEL AND HOW THINGS HAVE BEEN WITH YOU DURING THE PAST 4 WEEKS. FOR EACH QUESTION, PLEASE GIVE THE ONE ANSWER THAT COMES CLOSEST TO THE WAY YOU HAVE BEEN FEELING.

HOW MUCH HAVE YOU BEEN BOTHERED BY EMOTIONAL PROBLEMS (SUCH AS FEELING ANXIOUS, DEPRESSED OR IRRITABLE)?

○ NOT AT ALL
○ SLIGHTLY
○ MODERATELY
◉ QUITE A LOT
○ EXTREMELY

NEXT    EXIT SURVEY

FIG. 8-22 amIhealthy.com™

DYNAMIC HEALTH SURVEY™

22. DURING THE PAST MONTH, HOW DEPRESSED (AT ITS WORST) HAVE YOU FELT?

○ EXTREMELY DEPRESSED
◉ VERY DEPRESSED
○ QUITE DEPRESSED
○ SOMEWHAT DEPRESSED
○ A LITTLE DEPRESSED
○ NOT DEPRESSED AT ALL

NEXT   EXIT SURVEY

FIG. 8-23

*amIhealthy.com*™

DYNAMIC HEALTH SURVEY™

GENERAL HEALTH™

23. DURING THE PAST MONTH, HOW MUCH OF THE TIME HAVE YOU BEEN IN LOW OR VERY LOW SPIRITS?

- ◉ ALL OF THE TIME
- ○ MOST OF THE TIME
- ○ A GOOD BIT OF THE TIME
- ○ SOME OF THE TIME
- ○ A LITTLE OF THE TIME
- ○ NONE OF THE TIME ( NEXT )    ( EXIT SURVEY )

*FIG. 8-24*

*amIhealthy.com*™

DYNAMIC HEALTH SURVEY™

24. DURING THE PAST 4 WEEKS, HOW MUCH DID PERSONAL OR EMOTIONAL PROBLEMS KEEP YOU FROM DOING YOUR USUAL WORK, SCHOOL OR OTHER DAILY ACTIVITIES?

○ NOT AT ALL
○ VERY LITTLE
○ SOMEWHAT
◉ QUITE A LOT
○ COULD NOT DO DAILY ATIVITIES

NEXT    EXIT SURVEY

FIG. 8-25

*amIhealthy*.com™

DYNAMIC HEALTH SURVEY™

25. DURING THE PAST 4 WEEKS, HOW MUCH OF THE TIME HAVE YOU CUT DOWN ON THE AMOUNT OF TIME YOU SPENT ON WORK OR OTHER ACTIVITIES AS A RESULT OF ANY EMOTIONAL PROBLEMS (SUCH AS FEELING DEPRESSED OR ANXIOUS)?

○ ALL OF THE TIME
◉ MOST OF THE TIME
○ SOME OF THE TIME
○ A LITTLE OF THE TIME
○ NONE OF THE TIME ( NEXT )    ( EXIT SURVEY )

DYNAMIC HEALTH SURVEY — REPORT FOR ANONYMOUS

# YOUR SCORES

REPORT DATE: MAY 10, 2000
AGE: UNKNOWN
GENDER: UNKNOWN
CONDITIONS: UNKNOWN

PHYSICAL HEALTH SUMMARY  36

```
        36
         ▼
30    40    50    60    70
WORST      US AVG.       BEST
```
YOUR PHYSICAL HEALTH SUMMARY SCORE IS VERY MUCH BELOW AVERAGE, TAKING INTO ACCOUNT THE MARGIN OF ERROR.

MENTAL HEALTH SUMMARY  33

```
     33
      ▼
30    40    50    60    70
WORST      US AVG.       BEST
```
YOUR MENTAL HEALTH SUMMARY SCORE IS VERY MUCH BELOW AVERAGE, TAKING INTO ACCOUNT THE MARGIN OF ERROR.

YOUR PROGRESS

| DATE | PHYSICAL HEALTH SUMMARY | MENTAL HEALTH SUMMARY |
|---|---|---|
| CURRENT: 5/10/00 | 36 | 33 |

- WE ENCOURAGE YOU TO BECOME A REGISTERED USER SO THAT WE CAN REPORT AND INTERPRET YOUR CHANGES IN SCORES OVER TIME.

? WHAT YOUR SCORES MEAN

BASED ON YOUR ANSWERS ABOUT YOUR HEALTH IN THE PAST 4 WEEKS, OUR RESEARCH SHOWS THAT:

COMPARED TO THE GENERAL POPULATION...
*PHYSICALLY, YOUR...*
- FUNCTIONING IS WORSE
- PAIN IS VERY MUCH WORSE
- PERFORMANCE OF WORK, HOME OR SCHOOL ACTIVITIES IS MUCH WORSE

*EMOTIONALLY...*
- BOTHERED MUCH MORE THAN MOST
- PARTICIPATION IN SOCIAL ACTIVITIES IS MUCH MORE LIMITED
- PERFORMANCE OF WORK, HOME AND SCHOOL ACTIVITIES IS LIMITED MUCH MORE

*OVERALL, YOUR...*
- RATING OF YOUR HEALTH IS MUCH WORSE
- ENERGY LEVEL IS MUCH LOWER

WHAT YOU SHOULD DO

- SCHEDULE TODAY, AN APPOINTMENT WITH YOUR DOCTOR TO DISCUSS THE IMPACT THAT YOUR PERSONAL AND EMOTIONAL PROBLEMS ARE HAVING YOUR LIFE.
- IN ONE MONTH, TAKE THIS SURVEY AGAIN TO CONTINUE MONITORING YOUR PROGRESS.
- BY SHOWING THIS REPORT TO YOUR DOCTOR OR OTHER HEALTH CARE PROVIDER, YOU CAN WORK TOGETHER TO MAKE SURE THAT YOUR PHYSICAL & MENTAL HEALTH ARE AS GOOD AS THEY CAN BE.

NOTE: THIS SURVEY IS NOT A DIAGNOSTIC TOOL. IT IS INTENDED TO SUPPLEMENT, BUT NOT REPLACE OR CONTRADICT THE ADVICE OF YOUR PERSONAL PHYSICIAN. IF YOU HAVE ANY QUESTIONS OR CONCERNS ABOUT YOUR HEALTH, IT IS ALWAYS A GOOD IDEA TO SEEK ONE-ON-ONE PROFESSIONAL MEDICAL CONSULTATION.

METHOD AND SYSTEM FOR HEALTH ASSESSMENT AND MONITORING

RELATED APPLICATION

This application is a continuation-in-part application of U.S. Provisional Application Ser. No. 60/209,105 filed Jun. 2, 2000, which is incorporated by reference in its entirety.

BACKGROUND OF THE INVENTION

The present invention relates to an assessment technique, which is conveniently practiced on a computer. The computer is either a 'stand alone' or connected to a computer network, such as a local area network (LAN) or the world wide web, which is frequently and interchangeably referred to as the Internet. Other devices, including wireless enabled devices, may also be utilized in the assessment technique. The technique is particularly useful in the evaluation of the health of one or more persons.

In the United States alone, over 100 million people have chronic health conditions, accounting for an estimated $700 billion in annual medical costs. In an effort to control these medical costs, many healthcare providers have initiated outpatient or home healthcare programs for their patients. The potential benefits of these programs are particularly great for chronically ill patients who must treat their diseases on a daily basis. However, the success of these programs is dependent upon the ability of the healthcare providers to monitor their patients remotely in order to avert medical problems before they become complicated and costly.

Prior attempts to monitor patients remotely have also included the use of interactive telephone or video response systems. Such interactive systems are disclosed in U.S. Pat. No. 5,390,238; U.S. Pat. No. 5,434,611; as well as U.S. Pat. No. 5,441,047. These systems, however, have many shortcomings. One disadvantage of these systems is that they either require a patient to call in to a central facility to be monitored or require the central facility to call the patient according to a rigid monitoring schedule. Typically, if the patients are required to call the central facility, only the compliant patients will actually call regularly to be monitored, thereby undermining the purposes of monitoring the patients as a prophylactic measure. The non-compliant patients will wait until an emergency situation develops before contacting their healthcare provider, thus defeating the purpose of the monitoring system as a prophylactic measure. If the central facility calls each patient according to a monitoring schedule, it is intrusive to the patient's life. As a result, resistance to such monitoring will grow over time.

Improvements to monitoring systems have been proposed in the art. Examples of such systems include the following:

U.S. Pat. No. 5,997,476 describes a networked system for communicating information to an individual as well as remotely monitoring that individual. The system includes a server and a remote interface for entering in the server a set of queries to be answered by the individual. The server is a web server, and the remote interface is a personal computer or remote terminal connected to the server via the Internet. The system also includes a remotely programmable apparatus connected to the server via a communication network, preferably the Internet. The apparatus interacts with the individual in accordance with a script program received from the server, and the server includes a script generator for generating the script program from the set of queries entered through the remote interface. The script program is received and executed by the apparatus to communicate the queries to the individual, receive responses to the queries, and transmit the responses from the apparatus to the server.

U.S. Pat. No. 5,897,493 also describes a monitoring system that remotely queries an individual using a central computer system, a server, and a workstation networked to the server presenting a set of queries to be answered by the individual. Specific applications of the monitoring systems are, however, not discussed in detail.

Additionally, certain systems and techniques related to the evaluation of health, and more specifically health and/or behavioral indicia, are described in the following:

U.S. Pat. No. 5,882,203 describes a method for detecting depression and its severity. A series of statements formulated to detect the presence and severity of depression are presented to a subject in a multiple item visual analog format. The subject's answers are given a numerical value and the total score is then normatively ranked to determine the presence and severity of the depression. The method is optionally practiced with the use of a computer.

U.S. Pat. No. 5,967,789 describes a system to help a person stop or modify an adverse habitual health-related behavior, such as smoking, weight control, stress management, etc., by following a calculated regimen to commence on a day to be selected by the person. The system comprises a computer and a series of customized visually perceptible messages establishing a customized regimen to aid the person in stopping or modifying the adverse habitual health-related behavior. The computer receives personal information about the person, which is relevant to the behavior, and makes use of expertly designed system software to provide customized messages in response thereto. The customized messages are in the form of a daily sequence measured relative to a day selected by the person for the regimen to begin. Each of the messages is arranged to be read by the person in a specific sequence on a daily basis and includes respective numerical indicia representing the number of days from the selected day to the day of the message. The messages are provided to the person in various ways. For example, an electronic communication medium, such as the Internet, e-mail, facsimile, etc., delivers the messages to the person on a daily basis. Alternatively, the system can generate the cards or sheets in hard copy form and deliver them to the individual in a more traditional manner. The system may update and modify these messages based upon information provided by the person. Moreover, the system may provide the messages to a support person to aid the person wishing to change his/her health-related behavior.

U.S. Pat. No. 5,961,332 describes a method and an apparatus for processing data indicating an individual's psychological condition, psychological states, concomitant physiological states, and states of dysfunction along with principles, theories and research data to generate a diagnosis and a treatment plan for the individual. The apparatus also includes a remote user interactive means for providing remote access to and functionality of the apparatus.

U.S. Pat. No. 5,954,510 describes an interactive goal achievement system and method to assist persons in achieving and learning to achieve self-determined, measurable goals over time, while collecting data from a user on the user's progress toward achieving the goals. The system computes metrics from the data, gauges the user's progress towards achieving the goals, and provides the user with performance feedback. Further, the system collects additional information from the user regarding the user's estimate of the likelihood of achieving the stated goals, while also computing a separate objective estimate of the user's likelihood of achieving the goals. Preferably, a computer-based system implements the method, receiving and storing all of the collected information, computing the metrics, and generating the performance in the form of a progress report. Additionally, any suitable input device, such as a touch-tone telephone, for example, can be used to enter data into the computer system, while any suitable output device, such as a facsimile machine, can be used to provide the performance feedback to the user.

U.S. Pat. No. 5,940,801 describes a microprocessor-based diagnostic measurement apparatus and method for evaluating psychological conditions. The compact microprocessor-based unit produces a video display that prompts a patient or user to interactively operate one or more switches. The system records and analyzes information during an interactive diagnostic assessment procedure, which it then provides to a doctor or other health care professional. Such information can be used to determine whether clinical therapy and/or medication may be required. For example, the system utilizes a game-like video display to measure various neuropsychologic indicia of Attention Deficit Hyperactivity Disorder and Attention Deficit Disorder.

U.S. Pat. No. 5,908,301 describes a method and device for modifying behavior. The device includes interactive pre-set and adjustable behavior modification tools, which are suitable for encouraging modification of various behaviors, such as reduced or increased food intake, tobacco use, and alcohol consumption. A user can select from a plurality of parameters to customize a program or accept the default program. The device monitors and, if selected by a user, adjusts any behavior sequence, including behavior actions and behavior intervals. If a user selects a preset program using the default parameters, then the device maintains no record of any behavior action or interval, and it selects, records, and adjusts all other programs automatically for the next behavior sequence. A display on the device shows the user the selected program and its operation. The device provides multiple output signals to alert a user when to begin the next behavior action; when the pre-determined number of behavior actions has been attained; when the pre-determined number of behavior actions is being exceeded; and a special alert signal. The device accepts and modifies, either automatically or manually, a user's intended goal and the rate at which the user desires to attain the goal. In relation to goal and rate, it accepts and modifies the user's physical condition at the start of each program, re-evaluating the progress and adjusting related programs accordingly.

U.S. Pat. No. 6,039,688 describes a therapeutic behavior modification program, compliance monitoring, and a feedback system. The system utilizes a computer to monitor a patient's behavior in achieving lifestyle changes necessary to maintain his or her health or recover from ailments or medical procedures. The system monitors the individual's compliance with the program by prompting the individual to enter health-related data, correlating the individual's entered data with the milestones in the behavior modification program, and generating compliance data indicative of the individual's progress toward achievement of the program milestones. The system's design revolves around a community of support, which includes a graphical electronic navigator, operable by the individual to control the microprocessor, for accessing different parts of the system.

U.S. Pat. No. 5,879,163 describes an on-line health education and feedback system using motivational driver profile coding and automated content fulfillment. An automated system and method provide customized health education to an individual at a remote terminal, which is directed to induce a modification in the individual's health-related behavior. The automated system includes a questionnaire generator for questioning the individual to determine his or her motivational drivers and comprehension capacity. A profile generator receives answers entered by the individual from the remote terminal and generates a motivational driver profile and a comprehension capacity profile of the individual. A translator receives clinical data relating to a current health condition of the individual and translates the clinical data, the motivational driver profile, and the comprehension capacity profile into a profile code. An educational fulfillment bank matches the profile code to matching educational materials and transfers the matched educational materials to the remote terminal. An evaluation program evaluates educational responses of the individual and provides profile updates for targeting subsequent educational materials to the individual based on the educational responses.

U.S. Pat. No. 4,627,818 describes a psycho-technological testing method and device. The method and device aid in determining the disposition, traits, and characteristics of human test subjects. The device formulates several sets of statements, each set being related to at least one trait. The device then divides the statements in each set into two groups that contain several pairs of complementary statements, each pair probing the same point from different perspectives. A test subject provides responses from a multiple choice menu. The device considers the responses on a group basis, and assigns a weight factor to each response. The device then uses templates, which contain assigned weighting factors for each response, to add up a score for each group of statements.

The prior art also includes certain systems and techniques for specialized evaluations relating to health care. Examples include the following systems:

U.S. Pat. No. 5,666,492 describes a computer based pharmaceutical care cognitive services management system and method. The system and method captures all of the value added by a pharmacist in a patient encounter by permitting multiple RARs (Reasons, Actions, Results) to be associated with a single SOAP (Subjective, Objective, Assessment, Plan). This system enables the pharmacist to financially recover for each analytical or counseling session and/or service provided to the user associated with a single transaction. The pharmaceutical care cognitive services management system and method also enables the efficient processing of interruptions to cognitive and counseling sessions. When a pharmacist receives an interruption in the nature of a patient telephone call, an in-person patient visit, or a call from a physician requesting a refill for a prescription, the pharmaceutical care cognitive services management system and method suspends the cognitive or counseling session for a first patient, processes the interrupt for the second patient, and upon completion of the processing of the interrupt for the second patient, resumes processing the cognitive or counseling session for the first patient.

U.S. Pat. No. 5,845,254 describes a method for objectively monitoring the performance of a group of health care providers. The method stores in-patient payment claim records, representative of in-patient health-care services performed for patients by the group health-care providers, and out-patient payment claim records, representative of out-patient health-care services performed for patients by the group health-care providers, in databases. The method then builds sickness episode data records from the in-patient payment claim records and the out-patient payment claim records. An objective severity adjustment analysis is then performed on the sickness episode data records to form severity-adjusted sickness episode data records. From the severity-adjusted sickness episode data records, a cost efficient performance level is determined for each individual health-care provider within the group and a qualitative performance level for the group as a whole.

The prior art also includes various surveys that are not necessarily practiced utilizing a computer or computer system.

*SF-36 Health Survey—Manual & Interpretation Guide*, written by John H. Ware, Jr., Ph.D. et al., and published by The Health Institute, New England Medical Center, Boston, Mass. (copyright, 1993) describes a protocol for an improved health assessment and evaluation technique. The guide includes a thirty-six question survey, which is useful in assessing general health variables. Many have cited the thirty-six question survey as providing excellent results notwithstanding its brevity as compared to other surveys.

"Dynamic Health Assessments: The Search for More Practical and More Precise Outcomes Measures" by John E. Ware, Jr., Jakob Bjorner and Mark Kosinski, published in the *Quality of Life* newsletter, No. 21 (January-April 1999) generally discusses a psychometric method for assessing indicia of ideal health status.

An article related to the SF-36 survey is "The MOS 36-Item Short Form Health Survey (SF-36)" by John H Ware Jr., PhD. and Cathy Donald Shelbourne, PhD, published in *Medical Care*, Vol. 30, No. 6, June 1992.

A further article related to certain computer testing algorithms is described at pages 103-135 of *Computer Adaptive Testing—A Primer* by Howard Wainer, et al. published by Lawrence Erlbaum Associates, Hillsdale, N.J. 1990.

While many of these systems, methods and surveys offer certain advantages, they are fraught with shortcomings, which curtail their utility as well as their popularity. One such shortcoming is the length of the tests or surveys. As is well known, a test or survey has to be statistically significant to be considered an accurate instrument in evaluating a patient or respondent. As is also well known in the art, a greater number of questions generally leads to more statistically significant results. However, while a long test or survey having a large number of questions may provide improved statistical accuracy, it also places greater burden on the patient or respondent. The patient/respondent becomes reluctant to participate in the survey, particularly when it is given at a periodic interval. This reluctance manifests itself in (i) the failure of the patient/respondent to take the survey at prescribed time interval; (ii) the failure of the patient/respondent to participate in the survey altogether; (iii) the omission by the patient/respondent of one or more questions, which, of course, detracts from the statistical accuracy of the test; and (iv) an overall inconsistency in the responses of the patient/respondent. For example, a subset of questions directed towards evaluating a very specific condition or area of interest, which are divided and scattered throughout the survey, might not receive consistent responses. This result is particularly true when a large number of questions separate the related questions. Again, inconsistent answers reduce the overall statistical accuracy of the survey, as well as its perceived validity.

A further shortcoming in these surveys is that they are often directed towards providing an objective evaluation of a patient and his/her health. This method of evaluation doesn't allow a patient to provide their own feedback as to their own perceived state of health, which can be a significant distinction. Although, the objective evaluation of the patient and his/her health provides the healthcare practitioner or healthcare provider with objective indicia as to the perceived state of the patient's health, it is not necessarily helpful in all instances to the patient in understanding his/her health status or progress during any particular time interval. That is, the objective survey results are not frequently presented in a meaningful fashion to the patient. Rather, many of these surveys are primarily directed to the healthcare provider or healthcare organization. A subjective survey is much more meaningful to the patient in understanding their own health status and progress over any time interval. Healthcare providers/healthcare organizations, however, rarely utilize such subjective surveys, and traditionally favor the objective types of surveys known to the art.

Another shortcoming relating to the systems, methods, and surveys, which are cited above, is the relevant inflexibility of the surveys, which are set out in a standardized form and need to be completed in total by the patient/respondent every time that the survey is taken. Thus, patient/respondent encounters the same burden every time that he or she responds to such survey.

Furthermore, the prior art tests and surveys are non-adaptive. Prior survey results of a patient/respondent, or a group of patients/respondents, do not affect the future surveys that they are given. As such, the later surveys do not provide for differentiation in the health status of a patient.

An additional problem in the prior art surveys is their inflexible modes of administration. The surveys generally consist of either the traditional paper-based type or a computer-based replica of the same. The traditional paper-based versions provide a series of questions on paper sheets or booklets for the patient/respondent. After the patient/respondent completes the survey, the administrators evaluate the responses. While cost effective, the format remains inflexible. In the case of the computer-based surveys, many of the prior art surveys are little more than computer-driven versions of the same paper-based surveys, which provide little or nothing in added flexibility.

A further shortcoming in many of the prior art surveys is that they are unsuited for self-administration by a patient/respondent. In the context of the objective surveys described above, the patient/respondent may be very capable of taking the survey and responding to the questions provided therein, but many of these surveys do not provide an immediate response that is readily understood by the patient/respondent by the conclusion of the survey. Thus, while the "objective" type survey may provide meaningful results to a medical practitioner or a health services organization, it is not particularly adapted as a self-monitoring instrument to a patient or respondent.

Accordingly, there is a real and continued need in the art for improved systems and methods for the monitoring and assessment of a patient's health.

There is also a need for improved health assessment and monitoring systems that provide more accuracy in assessing and/or monitoring a patient's health, and that can be flexibly administered to one or more subject respondents/patients.

Further, there is a need for such systems as aforesaid that are less burdensome to administer to a patient than prior art systems.

There is also a need for such systems as aforesaid that are less burdensome on patients in their effort to participate in such systems.

It is appreciated that these are but representative of certain needs in the art which various aspects of the present invention address and provide.

OBJECTS AND SUMMARY OF THE INVENTION

Therefore, it is an object of the present invention to provide an improved system that overcomes the shortcomings of the prior art. Accordingly, the present invention provides a system for remotely monitoring patients and for communicating the results of such monitoring to the patient and, optionally, to others.

It is another object of the invention to provide a system as aforesaid which provides flexible and dynamic querying of patients with regard to their health or other personal indicia.

It is another object of the invention to provide a system as aforesaid which allows for monitoring of one or more patients whereby the monitoring method presents a reduced burden to the patient.

It is another object of the invention to provide a system and method whereby various aspects relating to the health of one or more patients can be monitored, and the results provided to the patient in a meaningful and immediate report.

It is another object of the invention to provide a system and method for monitoring, wherein the system and method as aforesaid includes an internalized method for evaluating the consistency of the responses received from the patient.

It is a further object of the invention to provide a system and method for monitoring, whereby the results obtained from such a monitoring session may be correlated with other evaluative scales known in the art.

It is a further object of this invention to provide a system and method for monitoring, whereby non-responsive answers to one or more questions may be estimated.

It is a further object of the invention to provide a useful method and system for monitoring of patients, whereby dynamic querying of the respondents provides for improved evaluation of specific areas of inquiry.

It is a further object of the invention to provide a system and a method for flexible and dynamic querying of a group of respondents with regard to both the individual and group responses, wherein the members of the group share a particular domain in common with each other.

It is a further object of the invention to provide an improved computer implemented system method for monitoring patients.

It is a further object of the invention to provide a computer-implemented method for generating a test or survey, administering said test or survey to one or more patients, evaluating the results of the tests or survey, and generating reports based on the results.

These and other objects and advantages will become more apparent after consideration of the ensuing description and the accompanying drawings.

BRIEF DESCRIPTION OF THE DRAWINGS

The following detailed description, give by way of example, and not intended to limit the present invention solely thereto, will be best understood in conjunction with the accompanying drawings in which:

FIG. 4 depicts a series of graphical representations of statistical assessment of two questions and responses thereto as provided by a group of respondents, as well as the graphical representations of a derived statistical assessment including a representation of consistency checking, and of error checking of the Assessment Method;

FIGS. 7-1 to 7-10 illustrate a representative test including a series of questions and possible responses and a report based on the questions and elicited responses; and FIGS. 8-1 to 8-27C depict a representative test which includes questions and possible responses, and a report based on the questions and elicited responses.

DETAILED DESCRIPTION OF THE EMBODIMENTS

Figure 1:
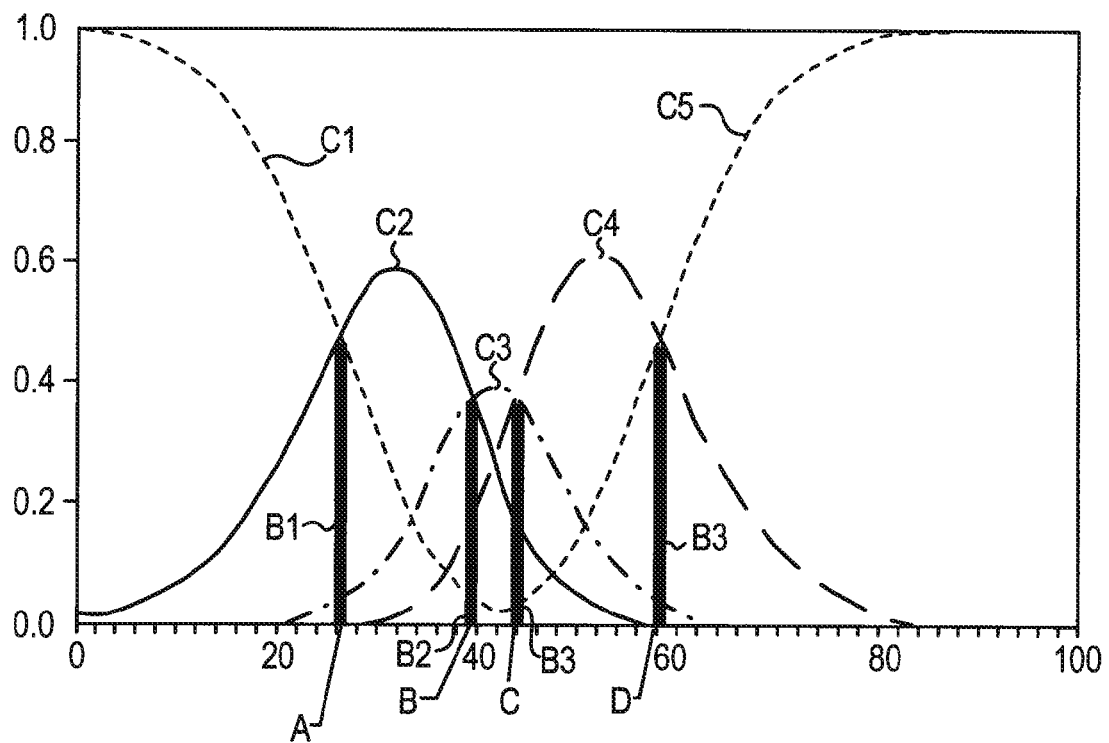
FIG. 1 depicts a graphical representation of the statistical assessment of a question and a response as provided by a group of respondents.

The definitions of the following terms as used in the specification are given by way of example to illustrate the concepts being discussed herein, and not intended to limit the terms solely to these definitions.

"Assessment Method"—The monitoring system being described herein.

"Test Subject"—The person taking the test. Such person may be referred to as a "subject respondent", and when the test relates to health related subject matter, may be referred to as the "patient".

"Testlet"—One or more questions primarily directed to evaluating the status of a Test Subject relating to a domain.

"Test"—One or more testlets which are used to evaluate one or more domains.

"Domain"—An aspect or condition experienced or perceived by the test subject sought to be evaluated by a test or testlet. By way of non-limiting examples, these can include various health-related measures such as severity of headaches, level of depression, degree of personal mobility, self-perceived status, general well being, etc. Other non-health related aspects or conditions perceived by a test subject may also be considered as valid domains as "customer satisfaction", and the like.

"Test Session"—A single episode of the administration of a test. Frequently, a plurality of test sessions are used by the test subjects regarding the test subject with regard to that test subject's perception of their personal condition or perceptions thereof relating to one or more specific domains.

"Subject Group"—A set of one or more test subjects who are participating in the Assessment Method in order to evaluate one or more domains which are common to each of the test subjects making up the subject group. The subject group can be a single individual test subject, but usually comprise two or more test subjects. By way of example, the subject group may be one or more test subjects who are associated with each other due to a common domain sought to be evaluated. The evaluation may relate to the individual test subject as well as for the subject group. Examples of such may include a group of headache sufferers, one or more persons suffering depression, and the like. A still further example of a subject group may be one or more test subjects who are associated with each other due to a common variable, and the desire to evaluate the responses elicited from a particular test subject as well as the whole subject group related to the variable. By way of example, such a variable may be a pharmaceutical composition which is being administered to one or more of the test subjects making up the subject group. In another example, the variable may be the practice of a specific therapeutic procedure upon one or more of the test subjects comprised in the subject group. As a still further example, the subject group may be one or more test subjects receiving specific health related services from a common provider, such as specific doctor, or a group of doctors, or organization such as health maintenance organization (HMO), pharmaceutical company, etc.

"Survey Respondent"—A person participating in a survey used in the test generation process of the Assessment Method.

"Device"—An article, apparatus, or instrument capable of presenting information to a test subject relating to the Assessment Method, which is desirably also capable of receiving a reply from the test subject. By way of non-limiting example, exemplary test devices include stand-alone computers, one or more computers connected to a network, one or more computers connected to the Internet, a computer terminal or other device that may be provided in an information kiosk, Internet appliances, hand-held computers also frequently referred to as "portable digital assistants" (PDA), Web-TV devices, telephones (both wired and wireless), bidirectional wireless communication devices such as bidirectional pagers and the like, as well as paper forms. Ideally the devices are two-way communications devices, particularly devices which include a display means (such as a cathode ray tube, flat panel display, and the like) or other means for prompting an input (such as audio devices, speech synthesizers, and the like) and an input device (such as buttons, keyboards, computer mice, touch pads or touch screens and the like.)

The present invention comprises several processes or modules, including, but not limited to, test generation, testing or administering, evaluating and reporting. These processes of the present invention as well as others are described hereinafter.

In the test generation process or module, the system collects data from a pre-existing data pool or database of questions and answers, statistically assesses the data, and forms a test for subsequent use in the testing process and process (or administration and evaluation modules). In accordance with an embodiment of the present invention, the system collects data by generating a survey of questions with a list of possible answers and providing it to one or more survey respondents in order to elicit their responses thereto. The individual questions of the survey should be similar to, or, preferably, the same as the tests to be subsequently utilized in testing and evaluation. Such similarity, or identity, in questioning ensures a high degree of relevance and statistical accuracy between the initial results garnered from the survey and the subsequent operation of the Assessment Method. The test questions can be of any form, and essentially can be directed towards any of a wide variety of subjects. Preferably, however, the survey includes one or more questions related to each of one or more domains which are sought to be evaluated by the Assessment Method. In accordance with an embodiment of the present invention, the questions have a graduated scale of possible answers associated therewith. A question is associated with scaled responses that have at least two possible answers (such as "yes" or "no"), and, preferably, have a graduated scale of potential responses (such as integer numbers within a range "1, 2, 3, 4, 5", or "very bad, bad, fair, good, or very good"). The reasoning behind the preference for a larger number of possible answers is that a plurality of potential responses to any test question provides a response that is more precise than a simple "yes" or "no." Where one or more of the test questions, preferably a majority of the test questions, have graduated scales of potential responses associated therewith, the Assessment Method provides more accurate results.

The survey comprises one or more questions evaluating one or more of the domains that are perceptible to the survey respondents. The possibility of domains varies widely, and covers all subjects of interest in the Assessment Method. The scope of a domain varies from general areas of interest, such as general health as perceived by a subject respondent, to more specific areas of interest, such as personal mobility. In such an example, personal mobility or depression may comprise a more narrowly tailored subset of the broad general health domain. Hence, a broader domain can comprise subsets corresponding to domains of narrower scope.

The generation of the form and content of the individual questions on a survey may vary from survey to survey. However, known-art surveys provide good guidance in fashioning useful survey questions and the associated possible responses. Of course, these survey questions and their answers must be relevant to the domain sought to be evaluated.

It is appreciated that the survey can be administered according to the prior art procedures as long as the collected data is available for subsequent statistical assessments. Naturally, selection of the survey respondents plays a key role in ensuring the accuracy of the survey. Preferably, the survey respondents should closely correlate to the expected test subjects of the Assessment Method.

In an alternative to the data collection process or module as discussed herein, the actual generation and administration of a survey can be skipped when a data pool of existing survey test questions and answers, relevant to the domains sought to be evaluated in the Assessment Method, are already available. Accordingly, the pre-existing test questions and answers can be utilized directly. However, the pre-existing survey questions and answers should be used only when they are relevant to the domains at issue.

In accordance with an embodiment of the present invention, the questions and answers are arranged into one or more groups, with each group designed to evaluate one or more domains. The generation of the survey might accomplish such arrangements, otherwise arrangement becomes a separate process within the data collection process or module. In one example, the system groups questions regarding perceptions of general health together, separating them from non-related health questions present in a survey. In another example, the system groups specific questions relating to physical functions and their extent together. More specifically, the system groups together questions to evaluate the degree of physical mobility, such as "can walk one mile without difficulty?", "can climb three flights of stairs without difficulty?", "can bend knees without stiffness or pain?", and the like. As can be seen in this group of questions, the primary focus of these questions is the domain relating to the physical mobility of a subject respondent. Such an arrangement of questions is desired if it is conducive to the administration of the test according to the Assessment Method. In certain instances, however, it may be undesirable to group such questions, particularly if it is believed that overall response consistency may be compromised by grouping of related questions.

According to another embodiment of the invention, the system and method includes statistical assessment of the questions and responses. That is, the system determines the statistical probability that a survey respondent at a particular scaled level or condition within the relevant domain will choose a particular answer to a question. The system uses known art techniques to calculate the requisite statistical probabilities. In addition, the system can normalize these determined results using known statistical methods against a larger population.

FIG. 1 provides an illustration of this concept with a representation of a graphical mapping of such statistical assessments. The ordinate axis is calibrated on a scale of 0-100, and is a numerical representation of a respondent's condition or status for the domain. Such scaled values may represent, for example, the degree of physical mobility, with a value of "0" representing immobility, and "100" representing complete unhindered mobility. The abscissa axis represents a scale of probabilities from 0.0-1.0. FIG. 1 also illustrates five curves (C1, C2, C3, C4, C5), each representing the statistical probability of the selection of one of the five graduated answers which were associated with the test question. The first curve, C1, corresponding to the probability that the first or "lowest" answer is selected, depicts only one half of its normal distribution curve as it is bisected by the abscissa axis where the ordinate scale reads "0". At the other end of the scale, at a reading of "100", the abscissa axis bisects the normal distribution curve shown as C5, corresponding to the probability that the highest graded answer to the test question is selected. Respectively, the curve according to C2 represents the normal distribution for the likelihood that a respondent would select the second lowest graded response, C3 represents the statistical likelihood that a respondent would choose the third (also the "intermediate") graded response to the test question, while C4 represents the statistical likelihood that a respondent would choose the fourth highest graded response.

In accordance with an embodiment of the present invention, the system utilizes the Rasch model, or in the alternative a statistical model based on Item Response Theory, to map responses to test questions obtained from the generated survey, i.e., statistical analysis. These statistical models are known to the art and are described in several reference materials on the subject.

Returning to FIG. 1, each curve depicts the statistical distribution of the responses to a single question elicited from the group of survey respondents. These curves can be used to predict the likelihood that a test subject, at a particular scaled level or condition within the relevant domain, would choose a particular graded answer when provided with the same test question. These curves are especially accurate when the test respondents are similar to the survey respondents. The results of the survey process within the Test Generation process or module are also useful for their predictive capabilities in the administration module and evaluation module of the present invention.

FIG. 1 also depicts four bars indicated as B1, B2, B3 and B4. These bars represent a perpendicular line extending from the ordinate axis to at least the intersection of the two adjacent curves, C1 and C2. According to this graphical representation, B1's intersection with the ordinate axis represents the value on the ordinate axis where C1 and C2 intersect. FIG. 1 depicts similar relationships for successive curves and successive bars. These bars define threshold values for each of the graded answers associated with the particular test question. For example, the value for the lowest graded answer falls between 0 and point A of the ordinate axis. Similarly, a response value for the second lowest graded answer associated with the test question falls between points A and B on the ordinate axis, while the third or "intermediate" answer falls between points B and C, the fourth answer between points C and D, and fifth and highest graded answer between point D and the end of the ordinate axis.

Such divisions provides a more precise numerical correspondence for how each of the five possible answers correspond to the scale of the ordinate axis. These divisions also establish ranges of the scale values from the ordinate axis that correspond to each of the possible answers to the question. As can be seen in FIG. 1, the probability of selecting one answer does not necessarily equate to the probability of selecting any other answer, providing a means for evaluating the discreteness of any test question considered alone and in conjunction with others.

Figure 2A:
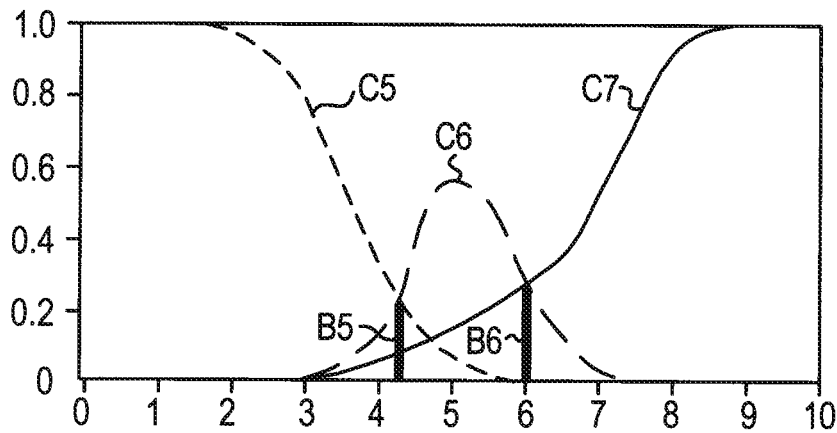
FIG. 2 depicts a series of graphical representations of statistical assessment of two questions and responses thereto as provided by a group of respondents, as well as the graphical representations of a derived statistical assessment.
Figure 2B:
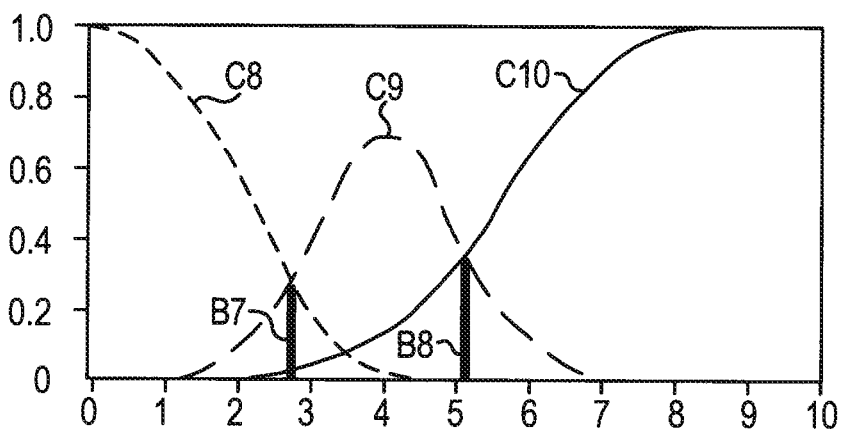
Figure 2C:
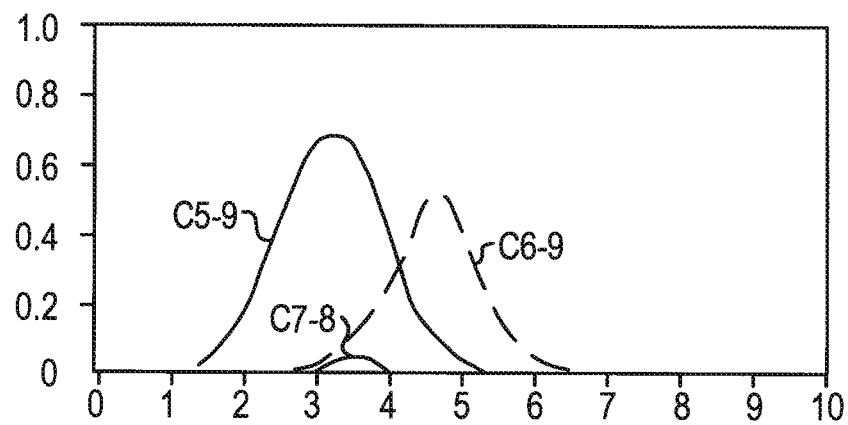

FIGS. 2A-2C further demonstrate the principles discussed in FIG. 1, showing that these principles are equally applicable to questions with either a lesser or greater numbers of associated responses. These figures also demonstrate that a lesser number of responses associated with a particular test question leads to a less discrete differentiation among the probabilities associated with the particular answers. More specifically, FIGS. 2A, 2B, and 2C depict a series of graphical representations of statistical assessment of two questions and responses thereto as provided by a group of respondents.

FIG. 2A depicts a mapping of the likelihood of selection amongst one of three possible responses to a test question. As in FIG. 1, the graduations on the ordinate axis correspond to the status or condition of the respondent within the relevant domain. In FIG. 2A, the abscissa axis indicates the relative probability of selection of one of the three possible responses. The normal distribution, i.e., the likelihood that respondent had selected amongst one of the three graduated answers is also depicted. Curve C5 indicates the probability that respondent selected the first or lowest scaled answer, curve C6 the second or "intermediate" answer, and C7 the third or highest scaled answer. Similar to FIG. 1, B5 indicates the value on the ordinate axis where the intersection of C5 and C6 occurs, while B6 indicates the value on the ordinate axis where lines C6 and C7 intersect.

It is appreciated that these bars in FIGS. 2A-2C act to divide the values scaled on the ordinate axis to provide a numerical value which corresponds to the range of scale values from the ordinate axis corresponding to each of the first graded answer, the second graded answer, or the third graded answer associated with a particular question. Again, a value from 0 to the intersection of B5 with the ordinate axis corresponds to a reply to the first, or lowest of the possible graded answers. Similarly, a response to the next, or intermediate possible answer associated with the test question, is assigned a value from the intersection of bar B5 with the ordinate axis to the intersection of bar B6 with the ordinate axis. A reply to the third or greatest of the three possible answers associated with the test question is assigned a value from the intersection of bar B6 with the ordinate axis to the end of the ordinate axis.

Again, as in FIG. 1, the mapped analysis of the answers as depicted on FIG. 2A represents the likelihood that a particular test respondent, with a condition in the domain corresponding to one of the scaled values depicted on the ordinate-axis, would select amongst the three possible responses associated with the test question. For example, someone with a perceived condition which corresponds with the midpoint of the ordinate axis in FIG. 2A, or the scaled value of "5", has a probability of 0.6 of selecting the second or intermediate answer, corresponding to curve C6. That same respondent is much less likely to choose the first response (approximately 0.1) or the third response (approximately 0.15).

Turning now to FIG. 2B, there is illustrated a graph depicting the mapping of the statistical analysis of the responses to a second question, which is related to the first question depicted in FIG. 2A. These questions relate to the same domain. Similarly, the second question has three possible responses. Again, the normal distribution of selecting among possible responses is shown. Curve C8 represents the probability that the respondent selects the first or "lowest" response, C9 the second or "intermediate" response, and C10 the third or "greatest" response. FIG. 2B illustrates two bars B7 and B8, indicating the corresponding values, also known as the "boundary values", of the scale on the ordinate axis to the intersection of C8 and C9 and the intersection of C9 and C10, respectively. Again, these bars, B7 and B8, divide the possible values of the scale of the ordinate axis into three regions, which encompass values corresponding to the three possible graded answers to the survey test question.

As noted above, the first and second questions test a common domain. The scaled values depicted on the ordinate axis in both figures represent the same values in the same domain, linking these questions together. Such a relationship established by commonality of the scale of the ordinate axis is preferred when grouping one or more questions together that are directed towards a particular domain. This grouping of questions, sharing of a common scale on the ordinate axis, and direction towards the same domain results in the creation of members of a Testlet.

The statistical analyses of the first and second questions, as illustrated in FIGS. 2A and 2B, provides a wide variety of further derived statistical information. Importantly, such analyses can provide derived information relating to the consistency of a test respondent's answers regarding a particular domain. Such analyses can also lead to the derivation of the status of a test subject within a domain, even when the test respondent has skipped one or more questions within a particular Testlet.

FIG. 2C illustrates the concepts of the importance of analyses within a Testlet. FIG. 2C depicts a statistical analysis that has been performed on responses relating to FIGS. 2A and 2B discussed above. Akin to both FIGS. 2A and 2B, the ordinate axis of FIG. 2C also shares the common scaling and values as those two prior figures. This identical ordinate axis ensures a commonality in the measurement or scaling of the domain being evaluated. However, while FIGS. 2A and 2B represent statistical analysis of questions and answers, FIG. 2C represents the statistical analysis of data derived from FIG. 2A and FIG. 2B. The abscissa axis in FIG. 2C indicates the relative probability of various combined replies. The three curves, C5-9, C6-9, and C7-8, indicate the probability of paired responses, based on one response to each of the questions from FIGS. 2A 2B.

The first curve, C5-9, indicates the cumulative probability that the respondent entered a selection of the first or "lowest" available answer to the first question corresponding to FIG. 2A, and chose the second or "intermediate" answer corresponding to the question associated with FIG. 2B. The fairly high probability that such a pair of answers to the first and second question derive from the survey indicates that, in any future test based on these questions, a test respondent selecting the same responses to the first and second questions is also reasonably likely.

The C6-9 curve represents the normal distribution of the likelihood of a second pair of responses, namely that a test subject selected the second or intermediate response to the question associated with FIG. 2A and the second or intermediate response with question associated with FIG. 2B. The normal distribution curve, as represented by curve C6-9, indicates the probability that the survey respondents selected the intermediate answers for both the first and second questions in the survey. Again, this curve also represents the likelihood that a test respondent would respond with the same answers to the same questions in a future test. Significantly, there is a visible degree of differentiation between the probabilities that the first set of answers, C5-9, versus the second set of answers, C6-9, would be chosen.

FIG. 2C also depicts a third curve, C7-8, which indicates the probability that the same survey respondent had selected the third or "highest" answer to the first question and the "lowest" or first answer to the second question. As can be seen from FIG. 2C, this curve, C7-8, is particularly small when compared to the normal distribution curves, C5-9 and C6-9. C7-8 illustrates the principle that it is highly unlikely that a respondent having a condition or status at a particular scaled level on the ordinate axis would have such a response pattern, namely choose an answer at one extreme of the scale of the ordinate axis, and yet on this next question, select an answer at the opposite end of the ordinate axis.

The discussion above with regard to FIG. 2C illustrates important principles key to the Assessment Method being taught herein. A statistical analysis of the questions and their responses reveals the likelihood of combinations of answers obtained in response to a combination of individual questions. Significantly, this information can be used for both error checking, i.e. to ensure the consistency of answers for a test respondent in a Testlet, as well as estimating answers to questions omitted by a respondent within a Testlet.

Although the discussion of FIGS. 2A-2C have been limited only to the probability of three pairs of possible answers, the principles described herein can be extended and performed on all possible combinations of answers to the questions. Similarly, where the Testlet comprises a greater number of questions, the statistical analysis can be performed on all of the questions and their possible answers. Further, it is appreciated that while the examples shown in FIGS. 2A-2C depict questions which include only three possible answers, there is no limitation the number of questions and the number of possible graduated answers to each question. The test questions having a greater number of possible graded answers generally provide a higher degree of differentiation among potential answers, and a finer degree of gradation.

In developing the figures outlined above, the present system analyzes the responses to each of the survey questions presented to the population of survey respondents on an individual basis in order to provide statistical data representing the likelihood that a respondent with a certain condition, as represented on the ordinate axis, would enter a particular response to a particular question. Then, the present system derives the likelihood of the combinations of responses in the Testlet from the statistical data for each individual question.

Using the information from the survey, the test generator of the present invention selects the questions to be included in the test for the Assessment Method. Preferably, the test generator divides the questions into groups, each group being directed towards assessing the status of the test subject with respect to a particular domain. For example, where a survey presented questions relating to different domains in a random order, the test generator can group them together for convenience. Such groups of questions directed toward a particular domain comprise the Testlets which can be subsequently administered.

In accordance with an embodiment of the present invention, the test generator optionally orders the questions within each group according to a sequence. This sequence can be arbitrary or based on statistical criterion, such as from the lowest to the highest probability of accurately predicting the actual status of the test respondent or conversely from the highest to the lowest probability of accurately predicting the actual status of the test respondent. It is appreciated that the sequence of the questions and answers provided in the Testlet generally does not limit the effectiveness of the Assessment Method.

In accordance with another embodiment of the present invention, the system establishes threshold limits, the minimum statistical probability which are considered to be acceptable for the valuation of the condition of a test respondent with respect to a particular score level and/or a particular domain. These limits can be arbitrary or based on a body of data, such as the survey questions and responses. Preferably, the threshold limit values determine the number of questions from a Testlet to be provided to a test respondent. For example, where the limiting value for a particular Testlet is relatively low, i.e., 50% probability, then it may be sufficient to query the test subject with a relatively small number of questions from that Testlet. Based upon the responses received from the test subject to each of the questions in the Testlet, the present system compares these responses against the statistical assessments previously generated in order to determine the cumulative probability of the status of the test respondent with regard to the condition being evaluated in the domain. When such a cumulative probability meets or exceeds the threshold limits, the testing from the Testlet is concluded. This process or module provides a means for optimizing or limiting the number of questions which in turn also reduce the burden imposed on the test subject. Conversely, where a high degree of statistical accuracy is desired with regard to analyzing the status of a test subject with respect to a particular domain, then the present system may need to use a larger number of questions from the Testlet during the test.

In accordance with a further embodiment of the present invention, the system includes the testing and processes for administration or evaluation modules. The questions of the test, which have been assembled in the test generation process or module, are presented to one or more test respondents on a device. Examples of such devices have been briefly mentioned above, and will be discussed in more detail herein. The device must be capable of presenting these questions in a discernible form as well as receiving the response to the particular question being elicited from the test subject. Subsequent to the receipt of such a response, the system compares the response against the statistically assessed responses to the same test question, which had been presented in the survey and/or presented to the test subject in one or more prior tests. The comparison includes an evaluation of the statistical probability of the appropriate assessment of the test subject within the domain being evaluated. If this statistical probability equates to or exceeds the threshold limits which have been previously assigned, then the Testlet is concluded. Alternately, if this threshold value is not attained, then the present system presents another question from the Testlet to the test subject. Again, the present system compares the response against the statistical assessment of the same (or similar) question from the test survey and/or a prior test. Thereafter, the system performs a statistical assessment based on the current responses to the test questions from the Testlet in order to determine the statistical probability associated with the combination of answers to the Testlet questions received thus far. This analysis may include the determination of the likelihood of the responses to each question for persons at a specific scaled value within the domain, as well as the statistical probability of combination of responses to these questions. Preferably, such statistical analysis of the combination of questions also includes the likelihood of consistent responses, as well as the likelihood of erroneous responses. Based on the results from such statistical analysis, the present system tests the probabilities against the threshold limit again, and if the value equates to or exceeds such a threshold limit, the Testlet is concluded. Otherwise the process repeats itself until the Testlet concludes.

Figure 3:
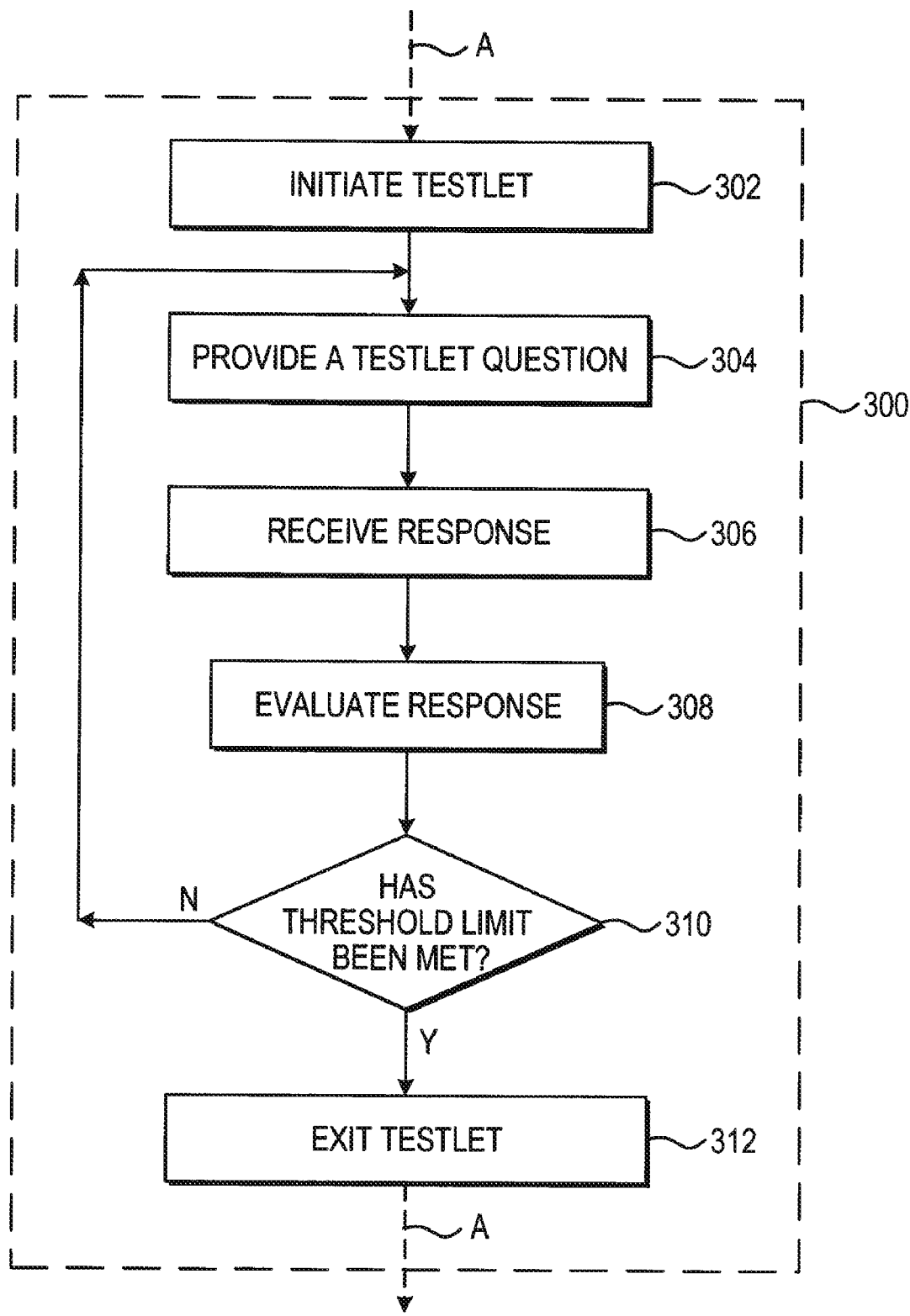
FIG. 3 depicts a flowchart of an aspect of the Assessment Method.

FIG. 3 depicts a flowchart of an embodiment of the Testing process, performed according to the Assessment Method being described herein. Functional Block 300, represented by dotted lines, indicates that the steps described therein form part of a larger process, or in the alternative, may be practiced in the absence of other prior or subsequent process steps.

In accordance with an embodiment of the testing process of the present invention illustrated in FIG. 3, step 302 represents the initiation of the Testlet. At step 302, the present system identifies the test subject and the test session, and it further identifies the group of questions related to a domain, i.e., a Testlet, to be presented to the test subject. This step also initiates access to the statistical information assessed from the survey and/or to questions and answers elicited from the test subject in a prior test session. In the next step 304, the system displays a Testlet question with its possible responses on the device. In step 306, the device receives the response to the displayed question. In step 308, the present system evaluates the received response by comparing it against the derived statistically assessed data. In step 310, the present system evaluates the statistical probability of a specific condition of the test subject with regard to the domain being tested and compares it against the established threshold limit. Where the limit has been satisfied, indicating an acceptable degree of probability has been attained, the present system may conclude the Testlet as shown in Step 312. Otherwise, the process returns to step 304 and repeates until the threshold limit is met. Upon exit from the Testlet in Step 312, the system stores data regarding the identity of the Testlet questions presented and responses elicited, as well as a statistical assessment of the group of Testlet questions performed.

FIG. 4 presents a more detailed description of the evaluation of the reception of responses described in Step 308 of FIG. 3. Turning now to FIG. 4, the figure comprises two sets of related figures. The first set comprises FIG. 4A-1, 4A-2 and 4A-3. The second set comprises 4B-1, 4B-2 and 4B-3.

FIGS. 4A-1 and 4A-2 represent the assessed statistical probabilities of responses elicited from survey respondents or test respondents from a prior test session. Each figure depicts a question having three possible responses, illustrating the likelihood of the selection of a particular response for respondents having a particular condition of the domain. FIG. 4A-3 illustrates the cumulative probabilities derived from the information related to FIG. 4A-1 and 4A-2. In FIG. 4A-3, curve C14 illustrates the cumulative probability that the test respondent will select the "intermediate" responses to the first and second question. An analysis of these figures reveals that the present system can identify consistency between test responses during the administration of a testlet and compare it to a threshold limit. For example, after two Testlet questions, a threshold limit may require a cumulative likelihood of at least 0.15 that the test respondent had a condition represented by the value "5" on the ordinate axis with a margin of error of ±−0.2. The test being administered in FIGS. 4A-1 to 4A-3 meets this threshold limit, and according to the flow chart the present system can exit the Testlet exit while the system stores the data for subsequent statistical assessment.

FIGS. 4B-1, 4B-2, and FIG. 4B-3 illustrate an embodiment of the error checking capabilities of the present inventive method. Similarly, the present system presents two test questions to a subject and establishes an error threshold limit, requiring that the cumulative responses to these two questions have a probability in excess of at least 0.05. If the subject selects the highest graded answer, C15, for the first question (FIG. 4B-1) and the lowest graded response, C16, for the second question selected (FIG. 4B-2) then C17 (FIG. 4B-3) represents the cumulative probability of such a combination of responses. In this example, the subject's responses have not yet met the error threshold, and the present system proceeds with the next step. This next step can vary widely according to the design of the Assessment Method. By way of non-limiting example, the next step may be a notification of this condition within the Assessment Method, the presentation of further questions from the Testlet in order to evaluate whether further Testlet questions are consistent, the generation of an error indicator such as a message that the answers are inconsistent, as well as other responses not recited here. The error checking capability ensures that intentionally misleading or fraudulent answers are not entered by the test subject in response to questions presented during a test.

In a testing session, the system identifies the test subject. Based on this information, the system compares the identity of a test subject against the identity of test subjects assigned to a particular subject group. If the test subject's identity is closely related to that of the group then the system identifies Testlets appropriate for this group and provides them to the test subject on an appropriate device, initiating the testing process or module. If the test subject does match up with a group, then the system may further solicit identifying information from the test subject. Matching a subject to a group is helpful in identifying the test subject for the purpose of tracking the progress of the test subject with respect to one or more domains when further test sessions are performed on the same test subject. If the test subject is not part of a subject group, then the system presents the subject with a number of options prior to the initiation of any Testlet. Preferably, these options correspond to the available Testlets which the test subject may choose.

Figure 5:
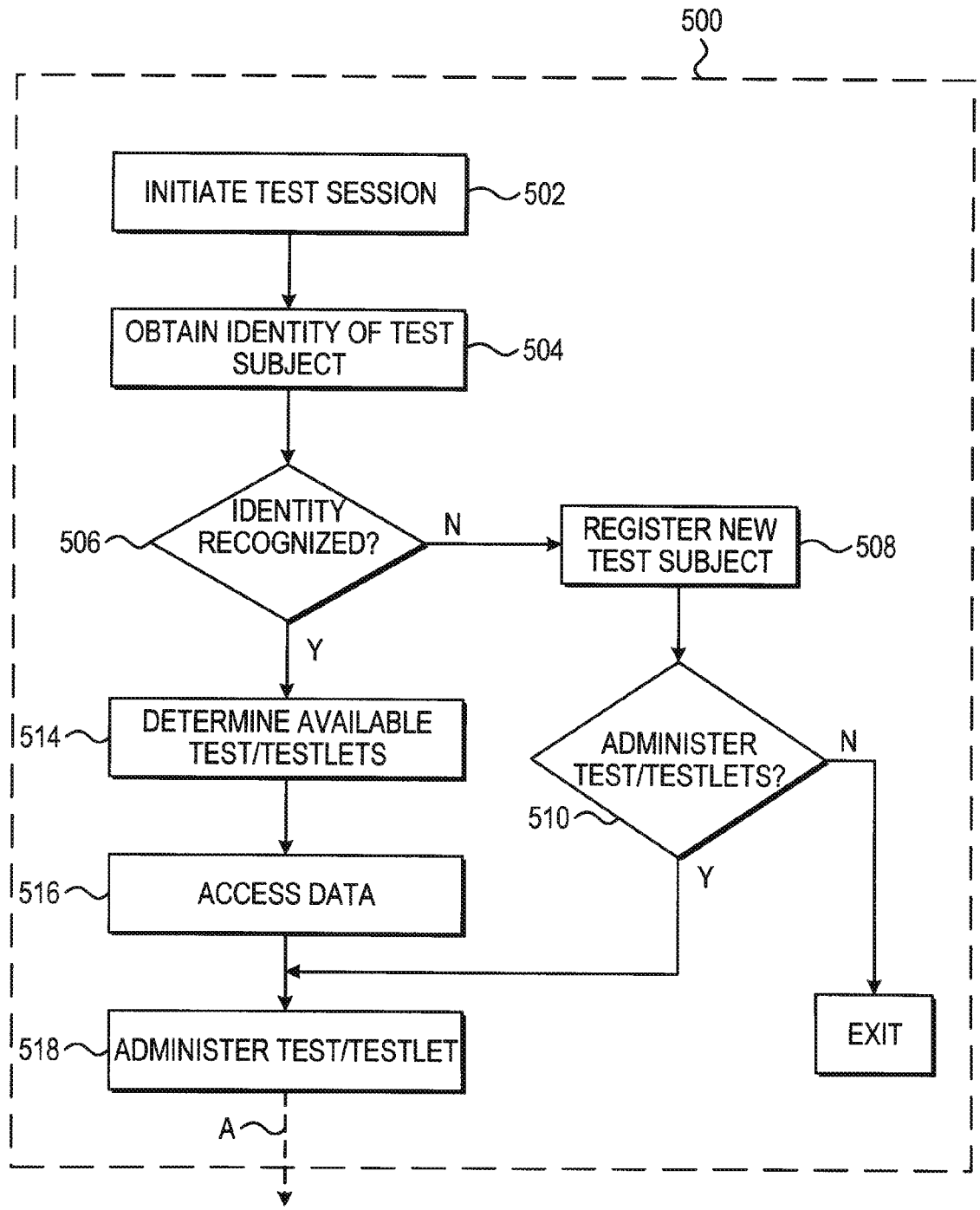
FIG. 5 depicts a flowchart of a further aspect of the Assessment Method.

FIG. 5 illustrates an embodiment of the testing process of the present invention. Block 500 comprises a plurality of steps relating to the initiation of a test session or administration module. Step 502 represents the initiation of the testing module to begin testing. During this initiation, the system accesses the questions and answers of Tests and Testlets as well as the derived statistical assessments thereof. In step 504, the system identifies the test subject. As has been noted above, the test subject may or may not have already participated in the Assessment Method, and may or may not be a member of the subject group. In step 506, the system compares the elicited information regarding the identity of the test subject against known prior participants of the health assessment methods and/or the identity of members of a subject group. If the system makes a match, then the system determines the available tests/Testlets for the identified test subject in step 514 and accesses the data from the prior test sessions of the matched group or individual in step 516. In accordance with an aspect of the present invention, if the test subject is a member of a subject group, then the system provides only those Testlets that conform to the conditions or limitations, if any, established for the test group. Otherwise, if the test subject is not a member of any subject group, then the system provides a selection of available Testlets without any restrictions or limitations. Thereafter, the system continues to step 518 to administer the Testlets to the test subject.

If the system fails to identity the individual then it proceeds to determine the identity of a new test subject in step 508, soliciting personal identification sufficient to uniquely identify the test subject in any future test sessions. If the test respondent provides such information, then the system establishes a suitable record or identifier. If the test subject refuses to enter sufficient identifying information then the system determines whether to administer any Testlets in step 510. If the present system concludes to administer no more Testlets then the present system exits the Assessment Method in step 512. Otherwise, the system administers the Testlet and continues the Assessment Method in step 518.

In step 516, dependent upon the identity of the test subject and the identity of the Testlets available to the test subject, the system accesses data relating to the derived statistical information of the questions and answers within each available Testlet (which may be based upon the information derived from the survey questions relating to a Testlet and/or responses elicited from the same test subject during a prior test session) for use in the subsequent administration of one or more Testlets. Thereafter in step 518, the system administers the Testlet. As will be appreciated from the previous discussions, the test may comprise the administration of one or more questions relating to one or more Testlets. Where a plurality of domains are to be evaluated via a plurality of Testlets, the system repeats step 518 until it completes the administration of all of the Testlets.

In a further embodiment of the testing process or module of the present invention, the system can establish an increased level of accuracy as well as inquiry towards one or more domains from a larger set of domains. For example, the system can establish a higher threshold limit to the domain of particular interest and/or diminish the threshold limit to the domains of lesser interest. In this way, the system streamlines the process by not requiring an unnecessary amount of additional questions for domains of reduced interest, while requiring a increased number of questions for a domain of particular interest. Such a process reduces the burden on the test subject without reducing the statistical accuracy of the Testlet.

In an embodiment of the present invention, the reporting process or module comprises the scoring and presentation of responses elicited during the testing process. According to one alternative, the system immediately presents the test subject with the results of one or more of the Testlets upon the conclusion of such Testlet. In another alternative, the system withholds the results until the conclusion of the test. The system can present these results in a simple form, such as a simple numerical readout, or in a graphical format such as curves, slopes, graphs, and the like. Preferably, the system presents the results in context. For example, it will present the scored Testlet results with a comparison to the average responses from one or more other test subjects who have taken the same Testlet. Such comparisons are most relevant when the test subject belongs to a group. As a further alternative, the system presents the results in comparison with historical results. Such historical results include, but are not limited to, the results from prior test sessions for the same Testlet by the same subject, the results of Testlets from the test having just been administered as compared to the cumulative results and historical variations of a group of test subjects, the results of the Testlets having just been administered as compared to both the results from prior art test sessions for the test subject, as well as the cumulative scores of a group of test subjects over the same time interval. In this manner, the system can present the test subject with relative changes or progress over a timed interval, such as a period of days, weeks, months, years, etc. The time intervals can vary and are not critical to the Assessment Method. Where, however, a regularly-timed interval is preferred, then it is also preferred that the test sessions occur approximately at the same corresponding timed intervals, i.e., monthly, weekly, daily, etc. In such a manner, uniform time intervals can be conveniently established. Such also facilitates monitoring of a test subject.

Figure 6:
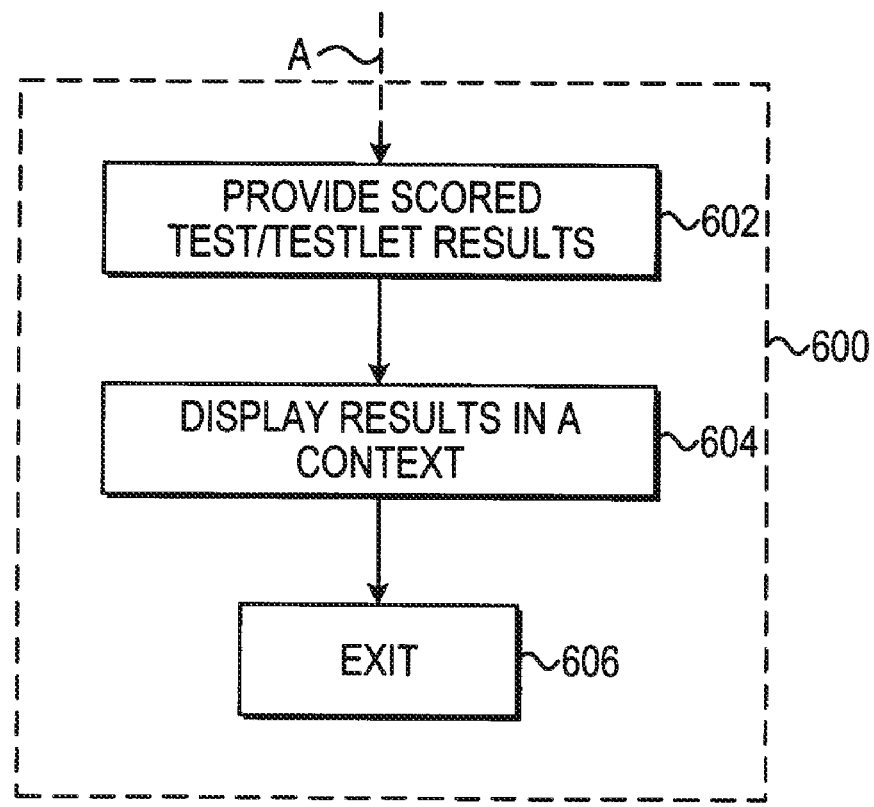
FIG. 6 illustrates a flowchart of a yet further aspect of the Assessment Method.

FIG. 6 illustrates the evaluation and reporting modules of the present invention in a simple flowchart. In step 602, the system displays the results from the tests having just been administered. The form and format of this display vary widely. Step 604 indicates that the system may present the results in one of many contexts. For example, the scores can be displayed against one or more different contexts. Also, the system can present the user or test subject with simple scores of the Testlets just administered and then present the test subject with various options, wherein the scores can be displayed against the background of historical data of the test subject, the test subject's previous score of same Testlet, other test subjects' scores, etc. It is appreciated that selectively viewing the scored Testlet results in various contexts by the test subject may advantageously aid in improved perception by the test subject of their perceived condition. That is, the system can allow the subject to choose the context of the presentation. Optionally, the system allows the subject to print or otherwise store the results. Thereafter in step 606, the system may exit the Assessment Method.

A particular advantage of the Assessment Method as described herein is in that unlike many prior art surveys which are inflexible and static, the test method of the present invention is dynamic. What is to be understood by static is that a survey is repeated for each test session and there is no possibility of altering the number of questions relating to a domain, or their sequence, or indeed the length of the survey. As has been noted above, such is particularly burdensome upon individuals, particularly where such individuals need to have the tests administered several times, such as in regular periodic intervals. Burdensome surveys are known to be more prone to errors, including misunderstanding and/or misanswered questions, as well as questions for which no responses have been provided. According to an aspect of the Assessment Method, during the administration of a test, based on the responses to questions elicited, the Assessment Method is capable of increasing or decreasing the number of questions presented to the test subject. As has been noted above, wherein a threshold limit has been established for a particular Testlet, then the Assessment Method need not present questions which exceed the minimum number of questions required in order to satisfy the threshold limit. The converse is also true, as wherein there may be a domain which is of particular interest or concern with respect to the test subject, then the threshold limits may be established at an increased level such that a larger number of questions from a Testlet need be presented prior to the conclusion of the Testlet directed towards assessing the status of the test subject with regard to their condition respective to a domain.

In accordance with an embodiment of the present invention, the Assessment Method establishes the test for one or more domains based on an increased level of accuracy as well as inquiry towards one or more domains from a larger set of domains. This can be done, for example, by establishing a higher threshold limit to the domain of particular interest and/or diminishing the threshold limit to the domains which are of lesser interest. The overall benefit of this is that wherein a test is directed towards evaluating several domains relevant to the test subject, then additional questions are not required for domains which are of reduced interest, while increased number of questions related to a domain of particular interest can be provided during the test. Such reduces the burden on the test subject without reducing the statistical accuracy of the Testlet.

A further embodiment of the evaluation or reporting process or module of the present invention comprises the provision for a method of estimating "skipped" answers to test questions. For example, when a test subject omits the response to one or more questions, then, based on the statistical analysis of the questions which have been properly responded to, the system calculates an estimate of the likelihood of the subject's response to the "skipped" question. More specifically, for a Testlet having a plurality of questions, i.e., five questions, directed towards evaluating a specific domain, but only four of the five questions have been responded to, a statistical analysis determines the correspondence between the four properly responded to questions and the fifth omitted question. If there is a sufficient level of consistency between these answers, namely a satisfactory degree of statistical probability that the answers to each of the four questions responded to correspond to a specific value, or limited range of values represented by the ordinate axis, then the system can provide a reasonable prediction that the skipped question would have been responded to with the available response which corresponds to that same ordinate axis value, or ordinate axis value range.

Further embodiments of the process or evaluation module of the present invention include the ability to utilize the results from the survey and particularly from the test administered and the resultant scales representative of their condition with different scales taken from different tests. The system utilizes various psychometric evaluations and scales to indicate the status of test subjects within certain domains. Prior art system have not been able to accurately interrelate and provide a correlation between the scales of these different psychometric evaluation techniques. In this embodiment of the present invention, the system uses the results of the Assessment Method with different scales and correlates between the scales utilized by different first psychometric analysis techniques. For example, the system presents a subject respondent with a plurality of questions in each Testlet. The system scores the responses to questions relative to the scales of both the first and second psychometric techniques. The system can establish a survey for each of the techniques and score the results on both scales simultaneously. At the conclusion of the test, and especially at the conclusion of a plurality of test sessions, the system can establish a correlation between these varying scales based on a derivation from the statistical analyses of consistent responses with respect to a subject's perceived condition relative to a domain. This is an invaluable aid in advancing psychometric analysis.

In an embodiment of the present invention, the system provides a further advantage by allowing the patient to self-administer a test. In another embodiment of the present invention, the system provides yet a further advantage through subject assessments of survey results. The system allows the subjects of the test to assign subjective measures to their responses based upon the individual subjective assessment and evaluation of their condition with regard to a domain and the scale of that domain. The system accounts for variations in this subjective assignment of values according to the domain, particularly when the initial survey questions and answers are statistically assessed and optionally, but in many cases, normalized against the overall population of the test subjects participating in the survey.

An advantage of the Assessment Method of the present invention relates to the type of reporting information which is provided to the test subject. As stated herein, many prior art surveys provide information which is of an objective nature, as these are frequently based on the objective observations of individuals observing the test subject. These are not necessarily based upon questions and responses elicited directly from the test subject without the intervention of such an observer. In contrast, the Assessment Method is based upon the subjective measurements which are assigned by the test subjects themselves who participate in the Assessment Method. These are believed to be particularly accurate as they are not based upon an external, imposed scale of a condition regarding a particular domain being evaluated, but are based upon the individual subjective assessment and evaluation of their condition with regard to a domain based on the scale of the domain. Variation in this subjective assignment of values according to a domain are accounted for in the Assessment Method, particularly when the initial survey questions and answers are statistically assessed and optionally, but in many cases, normalized against the overall population of the test subjects participating in the survey.

A still further important feature of the Assessment Method lies in the presentation of the Testlet scoring results. As has been discussed above, the data collected from test subjects is based on subjective data, i.e., their own perceptions and not based upon the perceptions of others viewing a test subject. According to particularly preferred embodiments, the information provided in the output of a report is presented in a fashion which is particularly meaningful to the test subject. This includes the forms and reports noted herein, such as those providing a historical assessment of the progress of a test subject with regard to one or more domains; a historical progress of the test subject with regard to one or more domains as against the historical progress of the subject group; and test score results from a particular test as compared to the test score results of prior test subjects having participated in the Assessment Method, being those participating in the survey, those participating in prior test sessions, or any combination of both of these groups. It is also foreseen that the content of information and/or format of the report can be established by the test subject, or by other individuals who may be participants or healthcare provider. It is appreciated that such modification permits for a wide degree of modification and contemplates the generation of customizable reports, and the ability to modify the report at any time by the test subject or other individuals. This provides a degree of flexibility to individuals who may be participating or monitoring the tests.

The Assessment Method described herein can be used over a broad range of subject matter.

Personal health monitoring is an area which is particularly advantageously practiced utilizing the Assessment Method described herein. Personal health monitoring can be used by test subjects to evaluate their own perceived condition relating to one or more domains relating to various aspects related to physical and/or emotional health. By way of non-limiting example, such domains include the impact of headaches, physical fitness, emotional fitness, depression, the impacts of asthma, as well as others not particularly elucidated here. One or more of these domains may be evaluated by the administration of Testlets having questions corresponding to each or one or more of the domains, or in the alternative, only a single domain, and a corresponding Testlet can be administered. While the test can be administered once, thereby the test subject can obtain a general measure of their responses relative to a larger population (such as of survey respondents and/or other test subjects), in an advantageous variation, the Assessment Method collects and stores the results of individual test sessions for the test subject. The test subject, upon repeating the test, may, over a period of time, perform several test sessions which can be used to assess the changes in the perceived status of the test subject with regard to these domains. As is noted above, this information can be graphically provided to the test subject. Further, it is contemplated that this information related to a test subject is maintained by the Assessment Method in a "health notebook". Such a health notebook is a visual representation of the collection of data relating to the test subject's responses to test questions which have been obtained, and analyzed during one or more test sessions. Such a health notebook is conveniently readily accessible from a device, and the results of the contents of the health notebook are readily printable for review and storage by the test subject apart from the device.

In accordance with an embodiment of the present invention, the Assessment Method or system assess the health status of a patient by providing a customized test that dynamically changes based on the patient's responses to the questions. The test module or process initially estimates a score, e.g., 50%, and generates a customized test having a number of questions relating to a health domain to be assessed. The health domain relates to a condition experienced or perceived by the patient, including but not limited to, severity of headaches, level of depression, degree of personal mobility, self-perceived status, effectiveness of a treatment, and general overall health. In accordance with an aspect of the present invention, the Assessment Method and system can be also utilized to assess non-health related conditions, such as, job satisfaction, opinion polling, personality test, customer satisfaction, human relationship, and the like. The administration module or process presents one question at a time to the patient. After each question, preferably after the patient's response to the question, the evaluation module or process calculates or re-estimates the score and a confidence level in the accuracy of the estimated score. The evaluation module or process estimates the score based on the various statistical analyses of the responses received from test subjects or other patients. Depending on the health domain, the evaluation module sets a pre-determined threshold based on the patient's estimated score. The evaluation module or process dynamically modifies the test until the estimated confidence level is within the predetermined threshold. That is, if the evaluation module or process determines that it can estimate the patient's answers to the questions in the test, it terminates the test since it has enough information to assess the patient's health status. This advantageously reduces the burden on the patient, since an assessment can be made without the patient answering all of the questions of the test or survey.

If the estimated confidence level is outside the pre-determined threshold, the evaluation module ranks the questions based on the estimated score and selects one of the questions that has not been administered or provided to the patient. Preferably, the evaluation module selects the question with the highest rank that has not been previously administered to the patient.

In another embodiment of the present invention, the system utilizes variables across a subject group to determine if any change in the test subject results from changes to the variable. By way of non-limiting example, variables can include: the assessed effect of a new pharmaceutical, drug composition or therapeutic method; a variation in healthcare providers (doctors, healthcare facilities such as hospitals, clinics, etc.), environmental changes such as reassignment of work or tasks to a test subject or patient, as well as others not particularly discussed herein. In such an embodiment, the system compares a body of data relating to one or more test subjects in a subject group prior to the introduction of the variable against the body of data collected from a test subject and/or subject group subsequent to the instruction of the variable. A comparison of the effects of the variable can provide a wide variety of useful information, including therapeutic benefits, therapeutic detriments, cost efficiency, change in perceived health status, change in perceived behavioral patterns, etc.

In accordance with an aspect of the present invention, the Assessment Method monitors one or more test subjects, particularly the individual responses of test subjects comprising a subject group. Such is particularly advantageous when each of the individual test subjects of a subject group are exposed to a common variable and, it is a function of the Assessment Method to determine if any change in the test subject results from the instruction of the variable. By way of non-limiting example, variables can include: the assessed effect of a new pharmaceutical, drug composition or therapeutic method; a variation in healthcare providers (doctors, healthcare facilities such as hospitals, clinics, etc.), environmental changes such as reassignment of work or tasks to a test subject or patient, as well as others not particularly discussed herein. It is to be understood that these are presented by way of non-limiting examples and that a far broader range of possible variables can be utilized in conjunction with the Assessment Method. In such an embodiment, a body of data relating to one or more test subjects in a subject group prior to the introduction of the variable may be obtained, and then compared against the body of data collected from a test subject and/or subject group subsequent to the instruction of the variable. A comparison of the effects of the variable can provide a wide variety of useful information, including the therapeutic benefits, therapeutic detriments, cost efficiency, change in perceived health status, change in perceived behavioral patterns, as well as others can be derived therefrom.

A significant advantage provided by the Assessment Method is in its use in the assessment of the costs as well as the benefits associated with the provision of health care related goods or services provided to one or more test subjects. As noted above, the Assessment Method is particularly useful in the monitoring of one or more test subjects, particularly individual responses of one or more test subjects comprising a subject group to a variable, where a change in health care related goods or service is being provided. The Assessment Method can be used to evaluate the costs and benefits resulting from the change in health care related goods or services to one or more test subjects in a subject group. The utility of the Assessment Method is broad and can be adapted to a wide range of specific applications. It is to be understood that virtually all health care related goods or services provided to patients or test subjects can be evaluated by the Assessment Method.

According to one example, the assessment of the efficacy of the substitution of pharmaceuticals in the treatment of a particular medical condition can be evaluated. Utilizing the Assessment Method, the efficacy of a first pharmaceutical for the treatment of a particular medical condition by a test subject, but preferably for a number of test subjects comprising a subject group, is established. Thereafter, a second pharmaceutical for the treatment of the same medical condition is substituted and the Assessment Method is used to evaluate the response in the treatment of the medical condition by the test subject, or number of test subjects comprising the subject group. Using the Assessment method, the individual responses of the one or more test subjects are evaluated, and information provided is used to evaluate the relative efficacies of the first and second pharmaceuticals for the treatment of the medical condition. Many of the advantages of the Assessment Method are realized in such an application, including reduced respondent burden, elicitation of responses based on the individual test subject's perception of their response to the first or second pharmaceutical, as well as the ability to provide reports to each of the test subjects following each test session. It is also an advantage of the Assessment Method that the costs of the first pharmaceutical and its benefits provided to the test subject, or number of test subjects comprising the subject group, can be compared to the costs of the second pharmaceutical and its benefits provided to the test subject or number of test subjects of the subject group.

According to a further example, the assessment of the efficacy of an experimental compound for use as a pharmaceutical composition for a particular medical condition can be evaluated. Such is particularly advantageous where evaluation of the experimental compound is required to obtain regulatory approval for the use of the compound for the treatment of the particular medical condition. Frequently, in such an evaluation, the efficacy of the experimental compound may be provided to a portion of the test subjects of a subject group, while other test subjects of the subject group are provided with a placebo. Using the Assessment Method, the individual responses of the test subjects are evaluated, and information provided is used to evaluate the efficacy of the experimental compound for use as a pharmaceutical composition for a particular medical condition, versus the efficacy of the placebo for use as in the treatment of the same medical condition.

A still further example, an assessment of the efficacy of the addition to or substitution of a healthcare provider can be evaluated for a group of patients which form a subject group. As noted above, non-limiting examples of healthcare providers include individual health care providers such as doctors, specialists, dentists, physical therapists, or other licensed healthcare providers, or groups of such healthcare providers such as those who have established "joint" practices, as well as larger healthcare providers or healthcare organizations such as hospitals and clinics which provide health care services to groups of patients. According to this application of the Assessment Method, the relative efficacy of a health care provider can be assessed. Further, the Assessment Method can be used to determine the relative efficacy of a health care provider as compared to at least as second health care provider for a group of patients who are test subjects in a subject group. This application of the Assessment Method is particularly valuable as the relative performance in the provision of health care goods and services by a healthcare provider to patients can be assessed and evaluated in a particularly meaningful way as the performance of healthcare providers is elicited from the test subjects, viz., patients. A further advantage of the Assessment Method is in its low respondent burden, and that it can be used to conveniently continually monitor the performance of healthcare providers both with respect to each other, as well as individually, over time. Comparisons between two or more healthcare providers can be accomplished by using the Assessment Method to assess the responses from a first set of patients being treated by a first healthcare provider and comparing these with the assessed responses obtained from a second set of patients being treated by a second healthcare provider, wherein the patients were from a common subject group, or wherein the first set of patients and the second set of patients were from two separate subject groups which nonetheless were substantially similar so to ensure that the Assessment Method and the results derived from its use are accurate to a satisfactory extent.

A yet further example contemplates the use of the Assessment Method in determining the efficacy of the use of a treatment regimen, such as a new or a specific surgical procedure, or the use of a new or specific therapeutic procedure or the use of a new or specific testing method or test device in the evaluation to prior practiced treatment regimens, testing methods or test devices. Similarly to the protocols outlined above, the Assessment Method can be used to determine the relative efficacy of new or specific therapeutic procedure or the use of a new or specific testing method or test device compared to prior or existing therapeutic procedures, testing methods or test devices for a group of patients who are test subjects in a subject group. This application of the Assessment Method in such an evaluation is particularly valuable as the relative performance of these new or specific therapeutic procedures, or new or specific testing methods or use of new or specific test devices can be assessed and evaluated in a particularly meaningful way as their performance and efficacy is elicited from the test subjects, viz., patients.

It is to be understood that these prior examples are provided as illustrative examples and are not to be understood as in any way limiting the broad scope of applicability of the Assessment Method in evaluating the provision of health care related goods or services provided to one or more test subjects.

A further advantage which may be provided by the Assessment Method is that the results and data obtained from the use of the Assessment Method may be used to facilitate in the selection of a particular regimen of treatment for a particular medical condition, where this selection can be made by either a patient, or the healthcare provider or both. The Assessment Method is a particularly valuable resource of information relating to the health of patients who participate as test subjects, and includes information relating to their health, as well as their responses to treatment regimens to particular medical conditions. From this information, a patient may evaluate their own health status and, if treatment for a particular medical condition is desired or necessary, the patient they may be provided with information relating to the efficacy of healthcare goods or services provided to other patients. This is particularly advantageous to the patient, healthcare provider or both in assessing the probable benefits and costs associated with available treatments for a particular medical condition, and is particularly useful in comparing the relative probable benefits and costs associated with various available treatments which may be used to treat the particular medical condition.

Still further, it is to be understood that while the Assessment Method described herein has generally been discussed with regard to evaluating factors regarding general health, it is to be understood that this is by way of illustration and not limitation and that other fields of use can equally benefit from the application of the principles of the Assessment Method. By way of non-limiting example, this may include customer satisfaction surveys for products or services. In such an example, the vendor/provider of such goods or services may elicit from customers or service recipient answers to survey questions. Therefrom they may derive a measurement of variations in satisfaction over a timed interval. In this way, the effect of changes in the goods or services being provided and their ultimate perceived effect as viewed by the purchaser or service recipient can be evaluated.

In a still further aspect of the invention, the Assessment Method may be used as a monitoring tool for remotely monitoring one or more test subjects with respect to long-term behavior or perceptions of behavior by the test subjects. Such can be wherein a group of employees comprise a subject group, and domains particularly relevant to the employee, such as perceptions of job satisfaction, general physical or mental health, and the like, are assessed over time. In this way, variations in the status of the members of the subject group, here employees, can be monitored and when a variation is noted, appropriate measures to correct the underlying causes can be taken. Such is particularly advantageous as frequently the cost of prevention as well as the course of identification is a small fraction of the ultimate costs needed to correct future more severe problems.

In a yet further aspect of the invention there is provided a method and apparatus by which to acquire, accumulate, analyze and apply pertinent information derived from one or more test subjects in order to define the nature and degree of an individual's status, particularly self-assessed or self-perceived with respect to one or more health related factors, viz., domains. Further, the method and apparatus of the present invention utilizes the data obtained therefrom may be used to objectively assess and recommend the treatment options which are available to the test subjects when such treatment is deemed appropriate. The method and apparatus of the present invention further provides a means by which to systematically assess the progress, process and outcome of the treatment options, methods, approaches and/or techniques which are being provided.

A further aspect of the present invention relates to an apparatus for performing the Assessment Method. This apparatus may be specially constructed for the operation of the Assessment Method, or it may comprise a general purpose computer as selectively activated or reconfigured by a computer program stored in the computer. Various general purpose machines may be used with programs written in accordance with the teachings herein. It is also possible that it may in certain instances be advantageous to construct more specialized apparatus to perform the required steps of the Assessment Method. Non-limiting examples of such machines include the devices described previously, as well as further machines and systems of machines described hereinafter. These non-limiting examples include stand alone' computer, or connected to a two or more computers on a computer network, such as a local area network (LAN) as well as larger networks such as the Internet.

In one aspect of the present invention there is provided an assessment and monitoring system which comprises a host computer facility supporting wired or wireless network delivery of user-relevant components, such as tests, and output such as reports of the Assessment Method to multiple remote user interface devices.

In another aspect of the invention there is provided an assessment and monitoring system which comprises a programmed general purpose computer which is programmed to operate the Assessment Method.

In another aspect of the invention there is provided an assessment and monitoring system which comprises computer-readable media which contains the instructions for use by a programmable general purpose computer necessary to operate the Assessment Method.

In another aspect of the invention there is provided an assessment and monitoring system which comprises one or more devices which are connected to a host computer facility which is programmed to operate the Assessment Method. The devices include without limitation computer terminals, general computers connected to the host computer facility, wireless devices including wireless telephones, two-way communications devices, or other devices which include an display means (such as a cathode ray tube, flat panel display, and the like) or other means for prompting for an input (such as audio devices, speech synthesizers, and the like) and an input device (such as buttons, keyboards, computer mice, touch pads or touch screens and the like.)

The Assessment Method according to the invention is conveniently adapted for implementation on physically compact, portable, user-interface devices such as small portable personal computers, and particularly hand held devices known as personal digital assistants. Those skilled in the art will understand that the system can readily be used on or adapted to other hardware platforms, for example, a desktop computer and can be expressed in different software interfaces from that shown in this specification, especially ones that use different input devices such as keyboards, touch pads or touch screens and the like.

The Assessment Method can be implemented in software, and can be provided for use for single-user operation on a stand-alone personal computer, or for multi-user operation on a network for use by a number of test subjects. Particularly useful are embodiments wherein a test subject is remotely administered a test session on a device, and the device is in communication with a host computer via a bi-directional wired or wireless connection. Examples of the former may include local area networks (LAN), wide area networks (WAN) as well as the Internet. Examples of the latter include connections wherein wireless means such as transmission via IR signals, microwave or radio-frequency communications are employed for at least part of the communications path between a device and the host computer. Thus a preferred embodiment of the invention comprises a host computer facility supporting wired or wireless network delivery of the tests and test sessions, as well as related information such as reports and the like, to multiple remote user interface devices. Such an embodiment is further preferred as a host computer facility can be conveniently used for the administration of tests in test sessions, statistical assessment of information regarding tests and test sessions, as well as related functions. One such function is operating as a central repository for maintaining records relating to test sessions, the identity of test subjects and subject groups. A further such function is operating as a central administration center wherein changes or modification to the content of the Assessment Method, particularly changes to the questions and format of the test and Testlets can be made.

The host computer facility provides data, or access to data, data processing and communications resources for test subjects operating the devices. The host computer facility can be a server or cluster of servers with associated data storage volumes, and at least one intelligent client providing access to the server or servers. The host computer facility can call upon a variety of external resources and functions as a marshalling and processing center for organizing resources for utilization by limited capacity devices. In a preferred embodiment it is a co-ordination point on a network for a device used in the administration of the Assessment Method. Optionally, the network accesses or includes a number of remote database sources providing access to elements both within and without the host computer facility.

The format of the test, test questions and reports may vary widely but desirably are arranged to provide a readily understandable presentation of information on the device upon which the test is administered. Desirably such a format for such information is provided on screens in a user-friendly format, and provides a user-friendly interface for presenting information and for providing a response to questions. Elements of such user-friendly interfaces are familiar to many computer users, such as activatable buttons, pointers, scroll bars, icons, arrow key, drop-down menus, windows and other screen symbols designed for actuation by a pointing device, for example, a mouse or trackball. More preferably, for embodiments implemented on a handholdabe computer, the pointing device is a pen or stylus. The Assessment Method itself can be programmed for operation in any suitable computer language (i.e., Pascal, C/C+/C++, assembly language, BASIC, etc.) and on any suitable operating system (i.e., UNIX, LINUX, Microsoft WINDOWS, Macintosh OS, etc.).

A further example of devices which find use with the instant invention are small handholdabe computers (sometimes referred to as "personal digital assistants" as well as "PDA"s). An example is the Pilot® handheld computer vended by Palm Inc. and the Visor® handheld computers vended by Handspring Inc., as well as the Hewlett-Packard Jomada® handheld computers. These handheld computers include a central processor unit, programmable memory, a display/input means, and a means for communicating with a computer or computer network. These latter means include a "wired" connection to a computer or computer network, as well as "wireless" communications capabilities such as radio wave or infrared wireless communications means enabling them to exchange data with a computer or computer network without the cost or inconvenience of hard wiring.

Pursuant to certain user-adaptive aspects of this invention, the screens are readily adapted to the test subject. This adaptive characteristic is a valuable benefit as the small and portable nature of the PDAs introduce great convenience in the administration of a test session, and the simplicity of interacting with such devices and providing responses to questions presented on the screens facilitate compliance with a periodic schedule of test sessions. The ease of use and suitability of the Assessment Method to such keyless or minimally keyed platforms, especially PDA's, is promoted by minimizing the need for actual text or data entry by the user and by emphasizing instead data selection by selection from among possible responses to questions. Preferred embodiments of the invention allow quick pen selection of data items through columnar "pick lists" of possible responses.

A further example of an interactive interface and delivery system suitable for use as a device for administration of the Assessment Method is a wireless telephone. A wireless telephone is suitable for use as a device as it provides bi-directional communication capabilities with a host computer or other computer, a keyboard or microphone suited for providing an input indicating selection of a response to a question, and a screen or speaker which can be used to provide questions to a test respondent in an audially and/or visually perceptible manner. Wireless telephones are also compact and portable and offer conveniences and benefits similar to PDA's discussed above.

A further example of an interactive interface and delivery system suitable for use as a device for administration of the Assessment Method may be an 'information kiosk'. Such an information kiosk includes a touch-sensitive display, keyboard or other input means so that the test subject may respond to questions provided during the test. In other operational respects such an information kiosk is similar to a conventional computer working independently of a network, or similar to a computer terminal or computer attached to a network but is available in public spaces and are intended for public access. Such might be also viewed as a 'public computer' or 'public computer terminal.' The benefits of such an information kiosk is that the test respondent need not be provided with a device in order to participate in the Assessment Method, but may participate from an information kiosk. Such lowers the overall costs which might otherwise be associated with the necessity of providing devices to test subjects, particularly where a larger number of test subject comprise a subject group. Further the public availability of such information kiosks may ensure better compliance with any regimen for which the Assessment Method may be utilized.

EXAMPLES

The following examples demonstrate an implementation of the Assessment Method described above.

The underlying survey data has been derived from the *SF*-36 *Health Survey* and the subject of the survey were directed towards assessing the overall general physical and emotional well being of a test subject. The device used was a IBM-compatible personal computer with a color monitor, keyboard, and mouse as input devices attached to the Internet.

The computer program operating in accordance with the Assessment Method was positioned at a location or remote from the device.

FIGS. 7-1 through 7-10 depict the display perceptible to the test subject, as well as the report for a test session. The test questions presented were responded to by the test subject with a perception that they are enjoying both excellent physical and excellent emotional and mental health. As can be seen from the figures, FIG. 7-1 indicates a time frame for the survey to the test subject, namely four weeks.

Figures 1, 7:
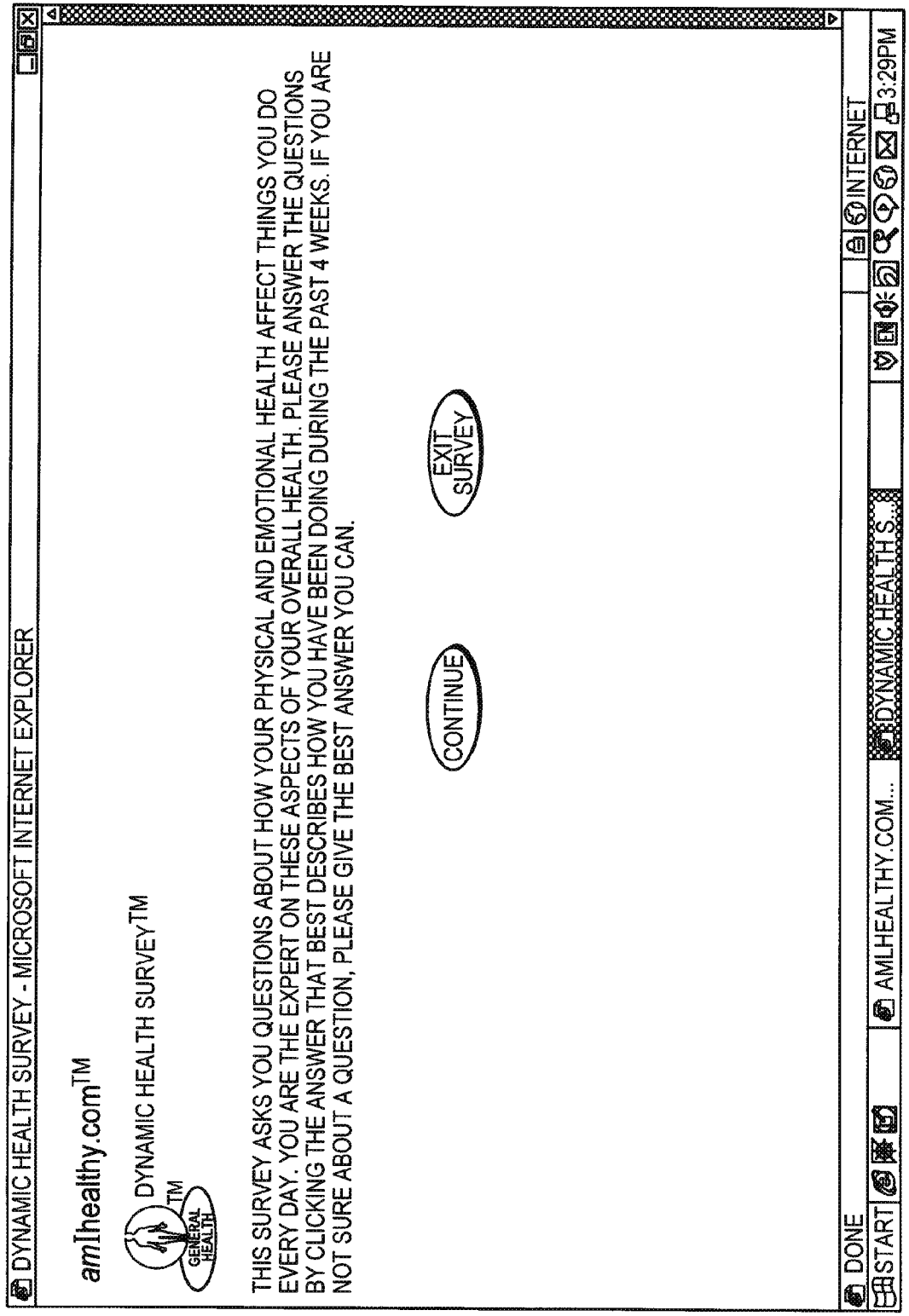

FIG. 7-2 represents the first question and the response provided by the test subject.

FIG. 7-3 represents the next question and the response provided by the test subject.

FIG. 7-4 depicts the subsequent question, wherein the timeframe for the test subject is repeated, as well as depicting the response elicited from the test subject.

FIG. 7-5 depicts the next question and the test subject's response.

FIG. 7-6 illustrates the next question, which also includes a repetition of the relevant timeframe (four weeks), as well as the response provided by the test subject.

FIG. 7-7 depicts the next question, as well as repeating the relevant timeframe for the test being administered and the response provided by the test subject.

Figures 7, 8, 9, 10, 10B:
Figures 7, 8:
Figures 8, 9, 10, 11, 12, 13:
Figures 8, 9, 10, 11, 12, 13, 14, 15, 16, 17, 18, 19, 20, 21, 22, 23, 24, 25, 26, 27, 27A:
Figures 8, 9, 10, 11, 12, 13, 14, 15, 16, 17, 18, 19, 20, 21, 22, 23, 24, 25, 26, 27, 27B:
Figures 8, 9, 10, 11, 12, 13, 14, 15, 16, 17, 18, 19, 20, 21, 22, 23, 24, 25, 26, 27, 28:
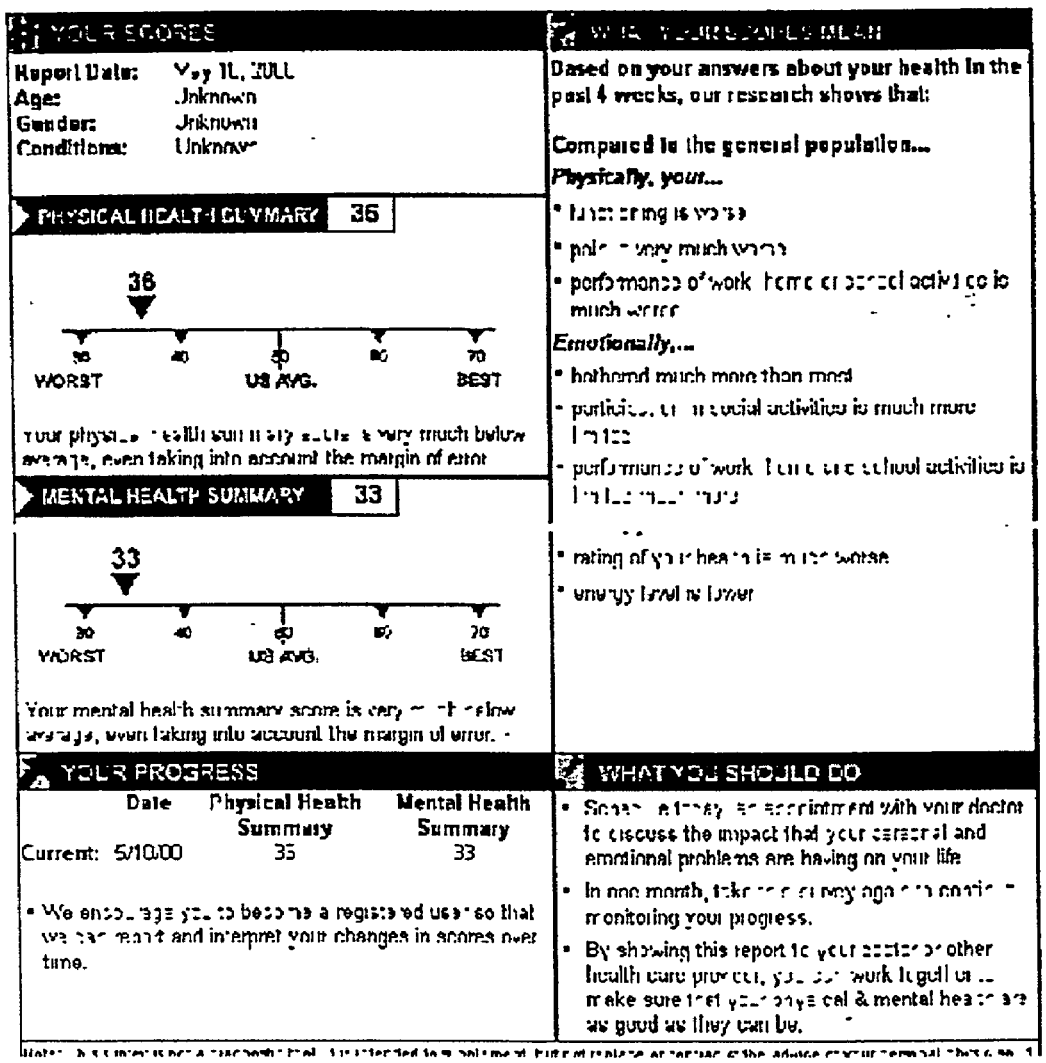

FIG. 7-8 illustrates the subsequent question provided, as well as the response provided by the test subject.

FIG. 7-9 illustrates the next question presented to the test subject and their response.

FIG. 7-10 illustrates the report presented to the test subject. The presentation of the report illustrates a wide variety of information which is particularly relevant to the test subject and provides regarding the test session having just been administered. The content of the report information is presented in a form and manner which is particularly meaningful to the test subject. As can be seen from an inspection of the report provided, there is provided to the test subject information regarding their perceived physical health, compared also in the context of the general physical health of the United States (as a population), their perceived mental health with regard also to that of the United States population, as well as an indicator of their progress. As this is the first administration of the test, a historical context has not yet been fully generated. The test also includes an interpretation of the scored test results in a straightforward manner which is particularly user friendly and the content is particularly relevant to the test subjects. The report also provides a suggestion for future action by the test subject, including the suggestion that the test should be repeated in three months time.

With regard to the questions presented in accordance with Example 1, it is significant to point out that subsequent to the receipt of only eight responses, the Assessment Method has provided an accurate scoring of the test subject in regard to several domains. These domains include the perceived physical health and the mental and emotional health of the test subject. More specifically, questions depicted on FIGS. 7-3 through 7-6 provides a question of a first Testlet directed towards evaluating the domain of general physical well being while the questions depicted on FIGS. 7-7 through 7-9 comprise the questions of a second Testlet directed towards evaluating the overall emotional and mental health perceptions of the test subject.

The degree of accuracy in evaluating the test subject was achieved subsequent only to eight questions which is particularly significant as a significantly reduced respondent burden was imposed upon the test subject. Notwithstanding the reduced respondent burden and the reduced number of questions, a level of statistical accuracy was comparable to that of the *SF*-36 *Health Survey* which in and of itself is amongst the shorter surveys known from the background art in the evaluation of such health concepts, i.e., domains.

Turning now to Example 2, therein is depicted in FIGS. 8-1 through 8-19 questions presented, responses elicited, and the final reporting of the test scoring of a test session wherein the test subject operated under the perceptions of very poor physical and very poor mental and emotional health. As can be seen by a review of the figures, the questions presented in FIGS. 8-2 through 8-19 are directed to a Testlet which focuses upon the self perceptions regarding physical functioning of the test subject. In contrast with the survey taken and completed in accordance with Example 1, the test subject here, operating under the perception of very poor physical functioning and physical health required that a greater number of questions in this Testlet need be answered. A greater number of questions in tests also provided to the Assessment Method, which in turn provides to the Assessment Method a large amount of data regarding the self perceptions of the test subject with respect to this domain. Such permits the Assessment Method to provide a more accurate measurement of the status of the test subject with regard to this domain, as well as providing a great amount of data to be stored and used in subsequent test sessions in order to evaluate the progress of the test subject with respect to this domain.

Similarly, with regard to the domain relating to self-perceived mental and/or emotional health, the Assessment Method provided seven questions requiring responses. Again, the test subject operated under the self perception of poor mental and emotional well being, and replied accordingly as indicated in FIGS. 8-20 through 8-26. Once again, this provided to the Assessment Method a greater body of response data which was used in the scoring of the Testlet, as well as score for subsequent use in future test sessions in order to evaluate the progress of the test subjects with regard to this domain.

FIGS. 8-27A-C depict the report generated immediately following the administration of the test. As can be seen by inspection, the report includes the generated score results for the test subject. The relative status of the test subject as determined by the assessment method in the context of the general U.S. population, as well as a user-friendly description regarding the scores obtained from the test session. The test report also includes a historical context indicating the progress of the test subject, but as this was the first test taken by the test subject, this information is circumscribed. The test report also provides a plain-language recommendation for next steps to be taken by the test subject. As can be seen by comparison of the length, as well as the nature of the individual questions presented in Example 1 versus Example 2 it can be seen that the Assessment Method dynamically alters the selection of subsequent questions based on immediately prior questions from which answers have been solicited. On the one hand in order to limit the burden of the respondent where there is a high degree of statistical probability in predicting the status of the test subject with respect to one or more domains only a few questions are presented. On the other hand, where the Assessment Method establishes that the test subject has potential problems with regard to one or more domains, presents additional, more focused questions with respect to those domains. Even so, the response burden to Example 2 was less than the burden for the *SF*-36 *Health Survey*, which comprises 36 questions, and which is not dynamic in nature. Notwithstanding the reduced number of questions, a comparable level of statistical accuracy was preserved in the scoring of the test subject's perceptions with respect to the tested domains.

While specific embodiments of the invention have been shown and described in detail to illustrate the invention, it will be understood that the invention may be embodied otherwise without departing from the principles of the invention and that various modifications, alternate constructions, and equivalents will occur to those skilled in the art given the benefit of this disclosure, Thus, the invention is not limited to the specific embodiment described herein, but is defined by the appended claims.

What is claimed:

1. A computer based system for assessing the health status or health care of a patient, comprising:
   a microprocessor configured:
      to generate a customized test, based on the patient's characteristics and one or more health domains selected by a patient or a health care provider, said test having a plurality of questions for said patient in accordance with said selected health domains;
      to administer said test by providing one question at a time to said patient; and
      to evaluate answers, after each question, provided by said patient to administered questions to estimate a score and a confidence level in the accuracy of said estimated score;
      to vary a threshold, after each question, as a function of said estimated score during administration of said test to said patient; and
      to dynamically modify said test being administered to said patient based on an answer provided to an immediately prior question if said estimated confidence level is outside said threshold;
   an interface associated with said microprocessor for presenting said test to said patient and for receiving said answers provided by said patient; and
   a database associated with said processor for storing said customized test, said plurality of questions; and said answers provided by said patient.

2. The system of claim 1, wherein said microprocessor is further configured to generate a report regarding the health status of said patient.

3. The system of claim 1, wherein said domain is a condition experienced or perceived by said patient.

4. The system of claim 1, wherein said microprocessor is further configured to rank said plurality of questions in accordance with said estimated score and select a question from said plurality of questions based on said ranking that has not been administered to said patient as part of evaluating answers provided by said patient.

5. The system of claim 4, wherein said microprocessor is further configured to select a highest rank question as part of evaluating answers provided by said patient.

6. The system of claim 1, wherein said microprocessor is further configured to terminate said administration of said test if it is determined that said estimated confidence level is within said threshold as part of administering said test.

7. The system of claim 1, wherein said microprocessor is further configured to generate said questions for said domain from a database having questions and answers pertaining to a plurality of domains as part of generating a customized test.

8. The system of claim 1, wherein said microprocessor is further configured to provide a list of possible answers for each question to said patient as part of administering said test.

9. The system of claim 1, wherein said microprocessor is further configured to statistically analyze said answers provided by said patient for errors or consistency as part of evaluating answers provided by said patient.

10. The system of claim 1, wherein said microprocessor is further configured to statistically analyze said answers provided by said patient for estimating non-responsive answers to said test as part of evaluating answers provided by said patient.

11. The system of claim 2, wherein said microprocessor is further configured to compare said answers provided by said patient with answers provided by other patients in said domain as part of generating a report regarding the health status of said patient.

12. The system of claim 1, wherein said microprocessor is further configured to administer said test to said patients over a network as part of administering said test.

13. The system of claim 2, wherein said microprocessor is further configured to generate said report over a network as part of generating a report regarding the health status of said patient.

14. The system of claim 12, wherein said network is one of the following:
   an Internet, an intranet, a telephone network, and a wireless network.

15. The system of claim 1, wherein said domain includes at least one of the following: severity of headaches, level of depression, degree of personal mobility, self-perceived status, effectiveness of a treatment, physical health, emotional health, impact of asthma and general overall health.

16. The computer based system of claim 1, wherein said microprocessor is configured to:
   administer said test before a variable is introduced, wherein said variable includes one of the following: a pharmaceutical, drug composition change, therapeutic method, health care provider, health care regimen, environmental change, lifestyle change, or work change; and further configured to readminister said test after said variable is introduced as part of administering said test; and
   wherein said microprocessor is further configure to compare resultant data obtained from each separate administration of said test by said administration module, wherein said resultant data is indicative of efficacy or impact of the introduction of said variable on said health status or health care of said patient.

17. The system of claim 1, wherein at least two domains are selected to be assessed.

18. A computer readable media comprising computer executable instructions for:
   generating a customized test, based on the patient's characteristics and one or more health domains selected by a patient or a health care provider, said test having a plurality of questions for said patient in accordance with said selected health domains;
   administering said test by providing one question at a time to said patient;
      evaluating answers, after each question, provided by said patient to administered questions to estimate a score and a confidence level in the accuracy of said estimated score; and
      varying a threshold, after each question, as a function of said estimated score during administration of said test to said patient;
   dynamically modifying said test being administered to said patient based on an answer provided to an immediately prior question if said estimated confidence level is outside said threshold.

19. The computer readable media of claim 18, wherein the step of dynamically modifying includes the step of terminating said administration of said test if it is determined that said estimated confidence level is within said threshold.

20. The computer readable media of claim 18, further comprising computer executable instructions for administering said test before a variable is introduced, wherein said variable includes one of the following: a pharmaceutical, drug composition change, therapeutic method, health care provider, health care regimen, environmental change, lifestyle change, or work change;
readministering said test after said variable is introduced; and
comparing resultant data obtained from each separate administration of said test, wherein said resultant data is indicative of efficacy or impact of the introduction of said variable on said health status or health care of said patient.

21. The computer readable media of claim 18, wherein at least two domains are selected to be assessed.

22. A computer based system for assessing the health status or health care of a patient, comprising:
a microprocessor configured:
to generate a customized test, based on a respondent's characteristics and one or more domains selected by the respondent or test provider, said test having a plurality of questions for said respondent in accordance with said selected domains;
to administer said test by providing one question at a time to said respondent; and
to evaluate answers, after each question, provided by said respondent to administered questions to estimate a score and a confidence level in the accuracy of said estimated score;
to vary a threshold, after each question, as a function of said estimated score during administration of said test to said respondent; and
to dynamically modify said test being administered to said respondent based on an answer provided to an immediately prior question if said estimated confidence level is outside said threshold;
an interface associated with said microprocessor for presenting said test to said respondent and for receiving said answers provided by said respondent; and
a database associated with said processor for storing said customized test, said plurality of questions; and said answers provided by said respondent.

23. The system of claim 22, wherein said microprocessor is further configured to terminate said administration of said test if it is determined that said estimated confidence level is within said threshold as part of evaluating said answers provided by said respondent.

24. The system of claim 22, wherein said domain is one or more health related or non-related conditions.

25. The system of claim 24, wherein said domain includes at least one of the following: severity of headaches, level of depression, degree of personal mobility, self-perceived status, general overall health, effectiveness of a treatment, job satisfaction, opinion polling, personality test, and customer satisfaction.

26. The system of claim 22, wherein said microprocessor is further configured to administer said test before a variable is introduced, wherein said variable includes one of the following: a pharmaceutical, drug composition change, therapeutic method, health care provider, health care regiment, environmental change, lifestyle change, or work change, and further configured to readminister said test after said variable is introduced as part of administering said test; and
wherein said microprocessor is further configured to compare resultant data obtained from each separate administration of said test, wherein said resultant data is indicative of efficacy or impact of the introduction of said variable on said health status or health care of said respondent.

27. The computer readable media of claim 18, further comprising computer executable instructions for generating a report regarding the health status of said patient.

28. The computer readable media of claim 18, wherein said domain is a condition experienced or perceived by said patient.

29. The computer readable media of claim 18, further comprising computer executable instructions for ranking said plurality of questions in accordance with said estimated score; and selecting a question from said plurality of questions based on said ranking that has not been administered to said patient.

30. The computer readable media of claim 29, further comprising computer executable instructions for selecting a highest rank question.

31. The computer readable media of claim 18, further comprising computer executable instructions for selecting said questions for said domain from a database having questions and answers pertaining to a plurality of domains.

32. The computer readable media of claim 18, further comprising computer executable instructions for providing a list of possible answers for each question to said patient.

33. The computer readable media of claim 18, further comprising computer executable instructions for statistically analyzing said answers provided by said patient for errors or consistency.

34. The computer readable media of claim 27, further comprising computer executable instructions for statistically analyzing said answers provided by said patient for estimating non-responsive answers to said test.

35. The computer readable media of claim 18, further comprising computer executable instructions for administering said test to said patients over a network, wherein said network is one of the following: an Internet, an intranet, a telephone network, and a wireless network.

36. The computer readable media of claim 27, further comprising computer executable instructions for generating said report over a network.

37. The computer readable media of claim 18, wherein said domain includes at least one of the following: severity of headaches, level of depression, degree of personal mobility, self-perceived status, effectiveness of a treatment, physical health, emotional health, impact of asthma, job satisfaction, opinion polling, personality test, customer satisfaction and general overall health.

38. A computer readable media comprising computer executable instructions for:
generating a customized test, based on a respondent's characteristics and one or more domains selected by the respondent or test provider, said test having a plurality of questions for said respondent in accordance with said selected domains;
administering said test by providing one question at a time to said respondent;
evaluating answers, after each question, provided by said respondent to administered questions to estimate a score and a confidence level in the accuracy of said estimated score;

varying threshold, after each question, as a function of said estimated score during administration of said test to said patient; and dynamically modifying said test being administered to said patient based on an answer provided to an immediately prior question if said estimated confidence level is outside said threshold.

39. The computer readable media of claim 38, further comprising computer executable instructions for terminating said administration of said test if it is determined that said estimated confidence level is within said threshold.

40. The computer readable media of claim 38, wherein said domain is one or more health related or non-related conditions.

41. The computer readable media of claim 40, wherein said domain includes at least one of the following: severity of headaches, level of depression, degree of personal mobility, self-perceived status, general overall health, effectiveness of a treatment, job satisfaction, opinion polling, personality test, and customer satisfaction.

* * * * *